US011787764B2

(12) United States Patent
Schnermann et al.

(10) Patent No.: US 11,787,764 B2
(45) Date of Patent: Oct. 17, 2023

(54) HEPTAMETHINE CYANINES FOR USE AS FLUORESCENT MARKERS OF THE BILIARY AND RENAL SYSTEMS

(71) Applicants: CHILDREN'S NATIONAL MEDICAL CENTER, Washington, DC (US); THE UNITED STATES OF AMERICA, AS REPRESENTED BY THE SECRETARY, DEPARTMENT OF HEALTH & HUMAN SERVICES, Bethesda, MD (US)

(72) Inventors: Martin John Schnermann, Rockville, MD (US); Peter C. W. Kim, Washington, DC (US); Jaepyeong Cha, Laurel, MD (US); Roger Rauhauser Nani, Fredrick, MD (US)

(73) Assignees: CHILDREN'S NATIONAL MEDICAL CENTER, Washington, DC (US); THE UNITED STATES OF AMERICA, AS REPRESENTED BY THE SECRETARY, DEPARTMENT OF HEALTH & HUMAN SERVICES, Bethesda, MD (US)

( * ) Notice: Subject to any disclaimer, the term of this patent is extended or adjusted under 35 U.S.C. 154(b) by 408 days.

(21) Appl. No.: 16/970,155

(22) PCT Filed: Feb. 14, 2019

(86) PCT No.: PCT/US2019/018057
§ 371 (c)(1),
(2) Date: Aug. 14, 2020

(87) PCT Pub. No.: WO2019/161091
PCT Pub. Date: Aug. 22, 2019

(65) Prior Publication Data
US 2021/0100919 A1  Apr. 8, 2021

Related U.S. Application Data

(60) Provisional application No. 62/631,390, filed on Feb. 15, 2018.

(51) Int. Cl.
A61B 5/00 (2006.01)
A61B 8/00 (2006.01)
A61B 10/00 (2006.01)
C07D 209/10 (2006.01)
A61K 49/00 (2006.01)
G01N 21/64 (2006.01)
G01N 33/533 (2006.01)
G01N 33/58 (2006.01)
C07D 403/12 (2006.01)
C09K 11/06 (2006.01)

(52) U.S. Cl.
CPC ......... C07D 209/10 (2013.01); A61K 49/006 (2013.01); A61K 49/0032 (2013.01); A61K 49/0058 (2013.01); C07D 403/12 (2013.01); C09K 11/06 (2013.01); G01N 21/6428 (2013.01); G01N 33/533 (2013.01); G01N 33/582 (2013.01); *G01N 2021/6439* (2013.01)

(58) Field of Classification Search
CPC .. C07D 209/10; C07D 403/12; C07D 209/12; A61K 49/0032; A61K 49/0058; A61K 49/006; C09K 11/06; G01N 21/6428; G01N 33/533; G01N 33/582; G01N 2021/6439
See application file for complete search history.

(56) References Cited

U.S. PATENT DOCUMENTS

| 10,280,307 B2* | 5/2019 | Schnermann | ........ C07D 209/12 |
| 10,876,003 B2* | 12/2020 | Schnermann | ........ C07D 209/14 |
| 10,961,193 B2* | 3/2021 | Schnermann | ........ G01N 33/582 |
| 2010/0056928 A1 | 3/2010 | Zuzak et al. | |
| 2011/0177007 A1 | 7/2011 | Rajagopalan et al. | |
| 2013/0296708 A1 | 11/2013 | Zuzak et al. | |
| 2013/0296709 A1 | 11/2013 | Zuzak et al. | |
| 2013/0296710 A1 | 11/2013 | Zuzak et al. | |
| 2015/0030542 A1 | 1/2015 | Singhal | |
| 2016/0144058 A1 | 5/2016 | Draney et al. | |
| 2020/0078474 A1 | 3/2020 | Draney et al. | |
| 2020/0085976 A1 | 3/2020 | Draney et al. | |

FOREIGN PATENT DOCUMENTS

| WO | WO-2004087766 A2 * | 10/2004 | ........ C07K 14/485 |
| WO | WO 2010/019515 A2 | 2/2010 | |
| WO | WO 2016/072984 A1 | 5/2016 | |
| WO | WO 2016/085884 A1 | 6/2016 | |

OTHER PUBLICATIONS

Taruttis et al. (PloS ONE 2012, 7, e30491, p. 1-6).*
Pu et al. (J. Biomed. Sci. 2009, 16, 1-11).*
Of Jensen et al. (Ann. Oncol. 2012, 23, 2341-2346).*
Zhang et al. (Int. J. Mol. Sci. 2017, 18, 1332, p. 1-14).*
Extended European Search Report dated Jun. 3, 2022 in corresponding European Patent Application No. 19754834.0 citing documens AA, BB, AO, AP and AX therein, 11 pages.
R. R. Nani et al., "Electrophile-Integrating Smiles Rearrangement Provides Previously Inaccessible C4' -O-Alkyl Heptamethine Cyanine Fluorophores", Organic Letters 2015, 17(2), 302-305.

(Continued)

*Primary Examiner* — Michael G. Hartley
*Assistant Examiner* — Melissa J Perreira
(74) *Attorney, Agent, or Firm* — Oblon, McClelland, Maier & Neustadt, L.L.P.

(57) ABSTRACT

Heptamethine cyanines for use as fluorescent markers of the biliary and renal systems are disclosed. Certain heptamethine cyanines exhibit renal system specificity, while others exhibit biliary system specificity. The compounds may be used for diagnostic purposes and/or for visualization of renal or biliary systems during surgery.

14 Claims, 18 Drawing Sheets

(56) References Cited

OTHER PUBLICATIONS

The partial Supplementary European Search Report dated Jan. 18, 2022 in European Patent Application 19754834.0, 11 pages.
Office Action dated Sep. 22, 2020 in corresponding European Patent Application No. 19754834.0, 3 pages.
International Search Report and Written Opinion dated May 15, 2019 in PCT/US2019/018057 filed on Feb. 14, 2019.
Wang et al., "Hemicyanine dyes linked with quarternary ammonium group: Near-infrared probes for the detection of nucleic acid", Sensors and Actuators B: Chemical, 2016, vol. 236, pp. 627-634.

* cited by examiner

| | FNIR-774 | FNIR-Ar-H_N-BS |
|---|---|---|
| Structure | | |
| 10mins Post-injection | | |
| Excretion into bile | +++(5mins) | +++(5mins) |
| Specificity (Biliary : Urinary) | 60:40 | 95:5 |
| Sulfonation | 4 | 2 |
| Quantum Yield, cLogP* *(calculated using Chemdraw) | 12%, 8.0 | 25%, 3.8 |

*FIG. 13A-1*

|  | ICG<br>(FDA Approved) | IRDYE800CW<br>(Commercially Available) |
|---|---|---|
| Structure | 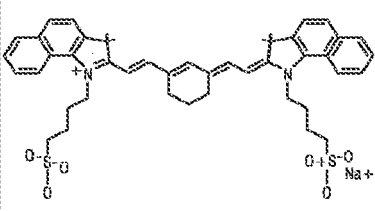 | 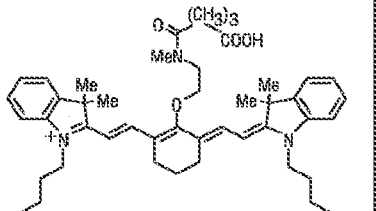 |
| 10mins Post-injection | 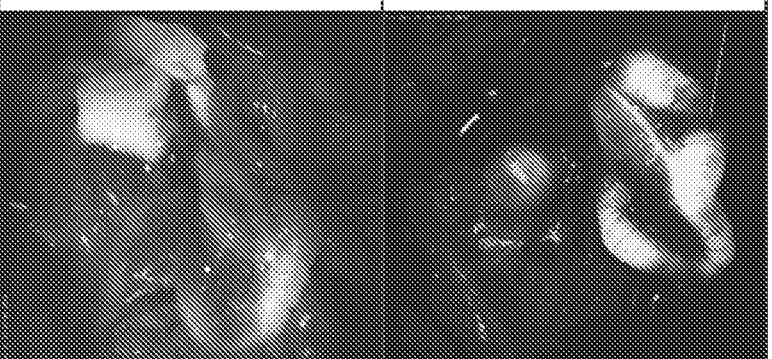 | |
| Excretion into bile | +(4hrs) | +++(5mins) |
| Specificity<br>(Biliary : Urinary) | 100:0 | 60:40 |
| Sulfonation | 2 | 4 |
| Quantum Yield, cLogP | 9%, 8-3.4 | 12%, -16.4 |
*FIG. 13B-1*

| FNIR-Ar-H_N-BS (Biliary Targeting) | Nac_Aryll-H_H-BS (Biliary Targeting) | UL-766 (Biliary Targeting) |
|---|---|---|
| 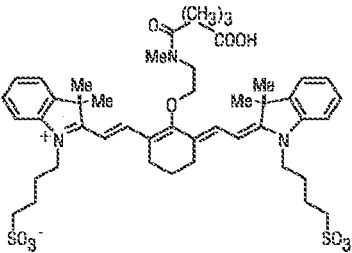 | 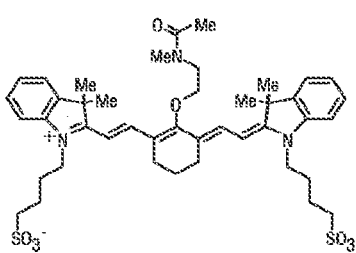 | 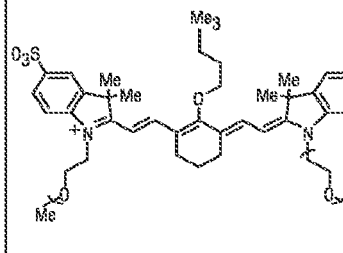 |
| 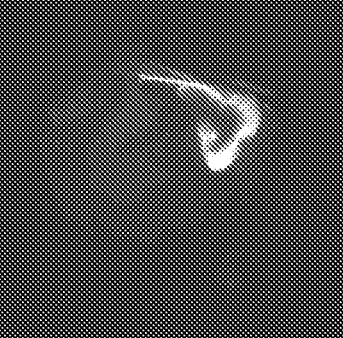 |  |  |
| +++ (5mins) | +++ (5mins) | +++ |
| 95:5 | 100:0 | 5:95 |
| 2 | 2 | 2 |
| 25%, -5.3 | 20%, -5.8 | 30%, -10.3 |
FIG. 13B-2

HEPTAMETHINE CYANINES FOR USE AS FLUORESCENT MARKERS OF THE BILIARY AND RENAL SYSTEMS

CROSS-REFERENCE TO RELATED APPLICATIONS

The present application claims priority to U.S. Provisional Application No. 62/631,390, filed Feb. 15, 2018, the teaching of which is hereby incorporated by reference in its entirety for all purposes.

STATEMENT REGARDING PRIOR DISCLOSURE BY THE INVENTORS

Aspects of this technology are described in an article "A chemically stable fluorescent marker of the ureter", published in Bioorganic & Medicinal Chemistry Letters, available online Feb. 24, 2018, which is incorporated herein by reference in its entirety.

BACKGROUND

Field of the Disclosure

The present disclosure relates to the use of heptamethine cyanine compounds and methods for use as fluorescent markers of the biliary and renal systems.

Description of the Related Art

Despite remarkable progress in molecular medicine, surgical interventions are nearly always carried out using only memory recall, visual and tactile cues. The identification and precise dissection or preservation of critical structures is central to the surgical process. Unintended injury results in short and long-term complications, prolonged hospital stays and health care costs. Adding insight through imaging is being explored with diverse modalities. Fluorescence-guided surgical methods provide real-time images using only relatively simple optical readouts. These methods are progressing toward clinical use in a variety of disease contexts. Most clinical efforts, however, use indocyanine green, a compound approved by the FDA over 50 years ago. To enable the broad adaptation of fluorescence-guided surgical methods, a new generation of dyes that address specific challenges in the field is needed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to the heptamethine cyanine compounds and methods for using the compounds as fluorescent markers of the biliary and renal systems.

According to an embodiment of the present disclosure, the heptamethine cyanine has a structure according to Formula I:

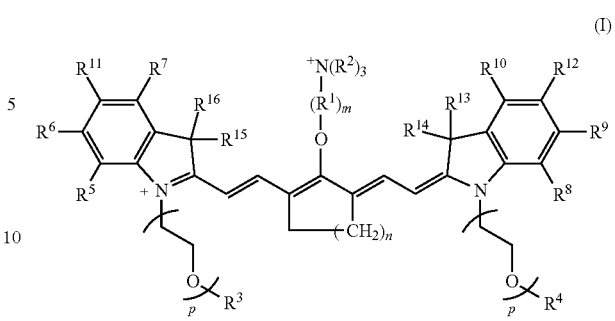

wherein m is 3, 4, or 5; n is 1, 2, or 3, each p independently is 1, 2, 3, 4, 5, 6, 7, 8, 9, or 10, $R^1$ is $-CR^a_2-$ where each $R^a$ independently is H, halo, optionally substituted alkyl, or optionally substituted aryl, each $R^2$ independently is methyl, ethyl, n-propyl, or isopropyl, $R^3$ and $R^4$ independently are alkyl, $R^5$ to $R^{10}$ independently are H or alkyl, $R^{11}$ and $R^{12}$ independently are sulfonate, H, or alkyl, and $R^{13}$ to $R^{16}$ independently are alkyl. In certain embodiments, the heptamethine cyanine has a structure according to Formula IA:

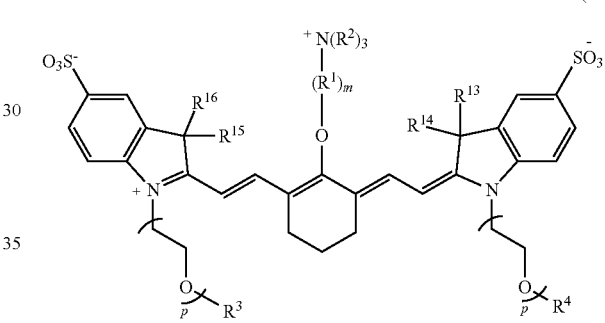

wherein $R^1$ is $-CH_2-$, m is 3, and p is 2, 3, or 4.

According to an embodiment of the present disclosure, the heptamethine cyanine has a structure according to Formula II:

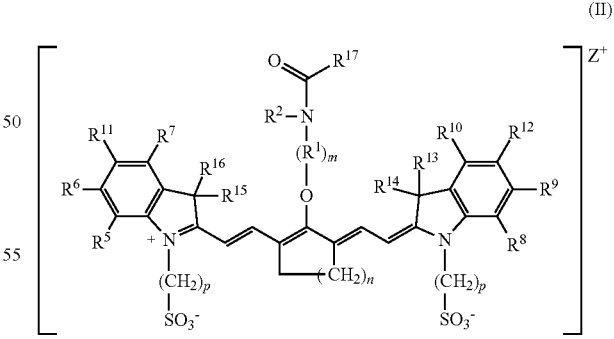

wherein m is 2, 3, 4, or 5, n is 1, 2, or 3, each p independently is 1, 2, 3, 4, 5, 6, 7, 8, 9, or 10, $R^1$ is $-CR^a_2-$ where each $R^a$ independently is H, halo, optionally substituted alkyl, or optionally substituted aryl, $R^2$ is $C_1$-$C_3$ alkyl, $R^5$ to $R^{12}$ independently are H or alkyl, $R^{13}$ to $R^{16}$ independently are alkyl, $R^{17}$ is $C_1$-$C_3$ alkyl, and Z is a monatomic ion. In certain embodiments, the heptamethine cyanine has a structure according to Formula IIA:

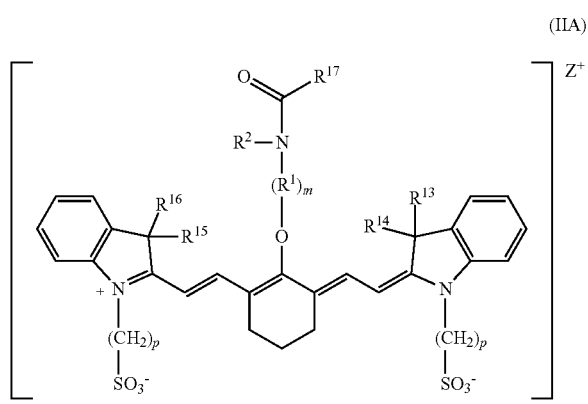

(IIA)

wherein $R^1$ is —$CH_2$—, m is 2, and p is 3, 4, or 5.

According to an embodiment, the present disclosure is further related to a method for visualizing at least a portion of a renal system or a biliary system of a subject including administering to the subject a compound according to Formula IA, Formula IIA, or

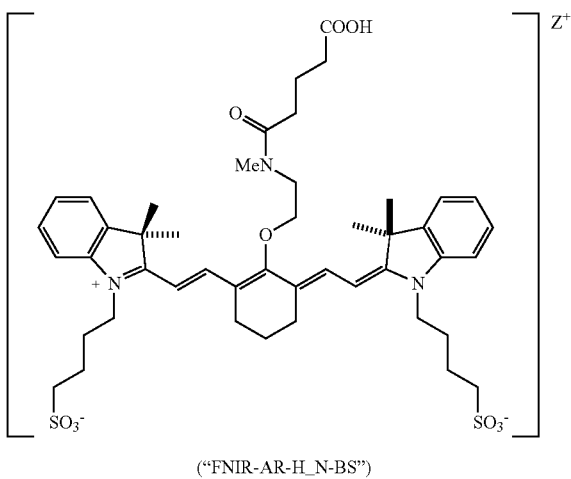

("FNIR-AR-H_N-BS")

wherein Z is a monatomic ion, subsequently administering a quantity of light to a targeted portion of the subject, wherein the quantity of light has a wavelength and an intensity sufficient to produce fluorescence of the compound, and detecting fluorescence in the targeted portion of the subject, wherein fluorescence indicates presence of the compound in the targeted portion of the subject. In some embodiments, the light has a wavelength or a range of wavelengths in the near-infrared range.

According to an embodiment of the present disclosure, the compound is a compound according to Formula IA, and the targeted portion of the subject comprises at least a portion of the renal system. In an independent embodiment, the compound is a compound according to Formula IIA or FNIR-AR-H_N-BS, and the targeted portion of the subject comprises at least a portion of the biliary system.

According to an embodiment, the present disclosure is further related to a method for visualizing at least a portion of a renal system of a patient, including administering Formula IA, subsequently administering a quantity of light to a ureteropelvic junction of the patient, wherein the quantity of light has a wavelength and an intensity sufficient to produce fluorescence of Formula IA, detecting fluorescence in the ureteropelvic junction of the patient, wherein fluorescence indicates presence of Formula IA in the ureteropelvic junction of the patient, and determining, based on the detecting fluorescence in the ureteropelvic junction of the patient, an obstruction of the ureter.

According to an embodiment, the present disclosure is further related to a method for visualizing at least a portion of a biliary system of a patient, including administering Formula IIA or FNIR-AR-H_N-BS, subsequently administering a quantity of light to the biliary system of the patient, wherein the quantity of light has a wavelength and an intensity sufficient to produce fluorescence of Formula IIA or FNIR-AR-H_N-BS, detecting fluorescence in the biliary system of the patient, wherein fluorescence indicates presence of Formula IIA or FNIR-AR-H_N-BS in the biliary system of the patient, and determining, based on the detecting fluorescence in the biliary system of the patient, bile leakage from a bile duct of the biliary system.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 13A-1 is a tabular representation of values of biliary excretion, biliary:urinary specificity, sulfonation, quantum yield, and cLogP values of heptamethine cyanine(s), according to an exemplary embodiment of Formula I and Formula II of the present disclosure;

FIG. 13A-2 is a tabular representation of values of biliary excretion, biliary:urinary specificity, sulfonation, quantum yield, and cLogP values of heptamethine cyanine(s), according to an exemplary embodiment of Formula I and Formula II of the present disclosure;

FIG. 13B-1 is a tabular representation of values of biliary excretion, biliary:urinary specificity, sulfonation, quantum yield, and cLogP values of commercially available dye(s), according to an exemplary embodiment of the present disclosure;

FIG. 13B-2 is a tabular representation of values of biliary excretion, biliary:urinary specificity, sulfonation, quantum yield, and cLogP values of heptamethine cyanine(s), according to an exemplary embodiment of Formula I and Formula II of the present disclosure;

DETAILED DESCRIPTION

Figure 1:
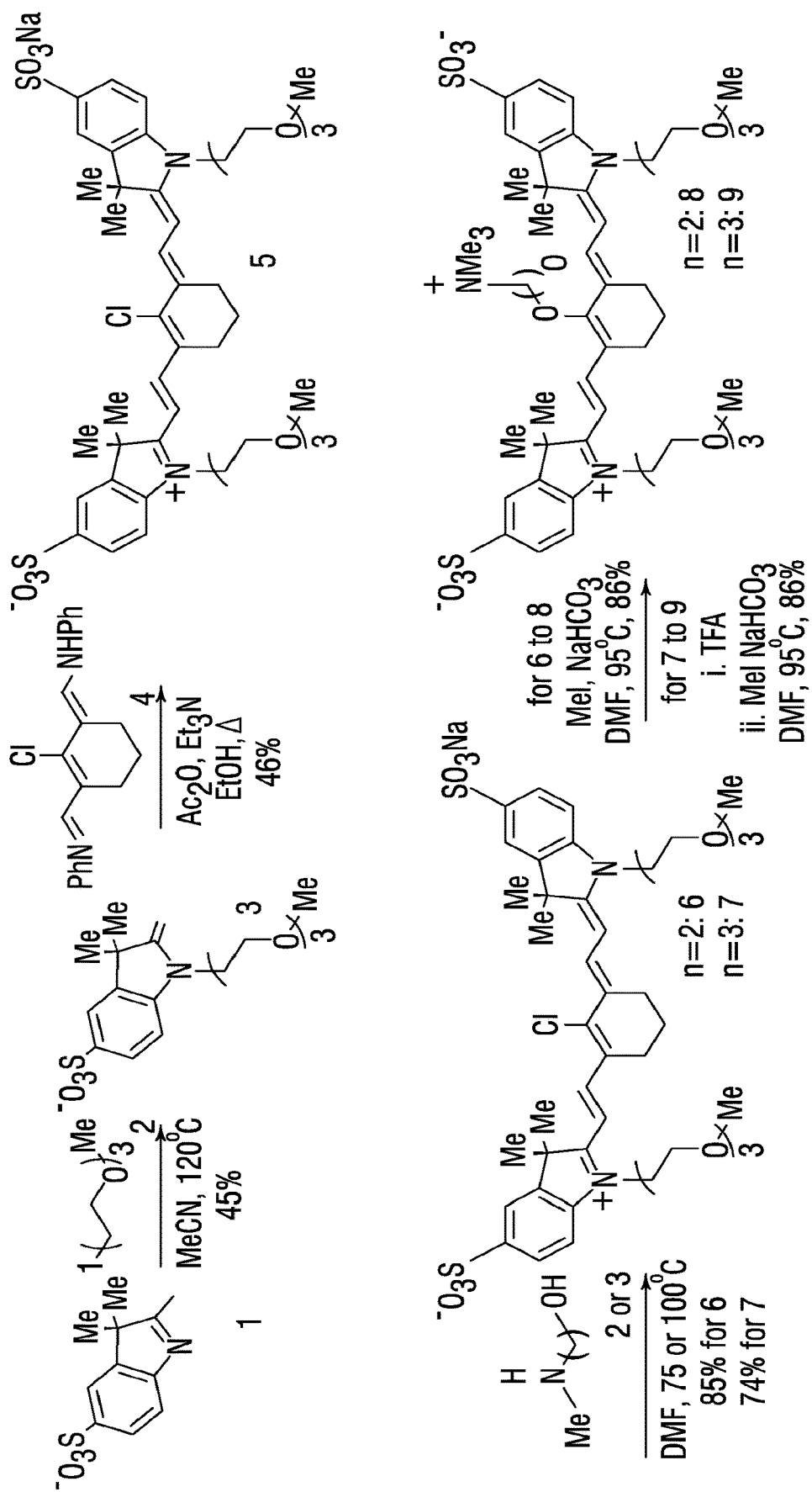
FIG. 1 is an exemplary synthesis scheme for making some embodiments of the disclosed heptamethine cyanine compounds according to Formula I.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

This disclosure concerns embodiments of heptamethine cyanines, and methods of making and using the heptamethine cyanines as fluorescent markers of the biliary and renal systems. Advantageously, some embodiments of the disclosed compounds are efficiently excreted with high specificity through either the renal system or the biliary system and exhibit good quantum yields, making them excellent candidates for in vivo visualization of the renal system or the biliary system.

I. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Alkyl: A hydrocarbon group having a saturated carbon chain. The chain may be branched, unbranched, or cyclic (cycloalkyl). Unless otherwise specified, the term alkyl encompasses substituted and unsubstituted alkyl.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, the term aryl encompasses substituted and unsubstituted aryl.

c Log P: A calculated or predicted log P value, where log P is the logarithm of a compound's partition coefficient between n-octanol and water: $\log(c_{octanol}/c_{water})$.

Effective amount or therapeutically effective amount: An amount sufficient to provide a beneficial, or therapeutic, effect to a subject or a given percentage of subjects.

Heteroalkyl: An alkyl or cycloalkyl radical containing at least one heteroatom, such as N, O, S, or $S(O)_n$ (where n is 1 or 2).

Near-infrared (near-IR, NIR): Wavelengths within the range of 650-2500 nm. Unless otherwise specified, the terms "near-infrared" and "NIR" as used herein refer to wavelengths within the range of 650-900 nm.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more conformationally-restricted cyanine fluorophores as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of disclosed conformationally-restricted cyanine fluorophores, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," *J. Pharm. Sci.* 1977, 66:1-19, which is incorporated herein by reference.)

Quantum yield: A ratio of the number of fluorescence photons emitted to the number of excitation photons absorbed.

Stereoisomers: Isomers that have the same molecular formula and sequence of bonded atoms, but which differ only in the three-dimensional orientation of the atoms in space.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, isocyano, isothiocyano, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Sulfonate-containing group: A group including $SO_3^-$. The term sulfonate-containing group includes $-SO_3^-$ and $-RSO_3^-$ groups, where R is substituted or unsubstituted alkyl, substituted or unsubstituted heteroalkyl, substituted or unsubstituted aryl, or substituted or unsubstituted heteroaryl.

Target: An intended molecule to which a disclosed conformationally restricted cyanine fluorophore comprising a targeting agent is capable of specifically binding. Examples of targets include proteins and nucleic acid sequences present in tissue samples. A target area is an area in which a target molecule is located or potentially located.

Tautomers: Constitutional isomers of organic compounds that differ only in the position of the protons and electrons, and are interconvertible by migration of a hydrogen atom. Tautomers ordinarily exist together in equilibrium.

II. Heptamethine Cyanines

According to certain embodiments of the present disclosure, the disclosed heptamethine cyanine compounds may have a structure according to Formula I, or a stereoisomer thereof:

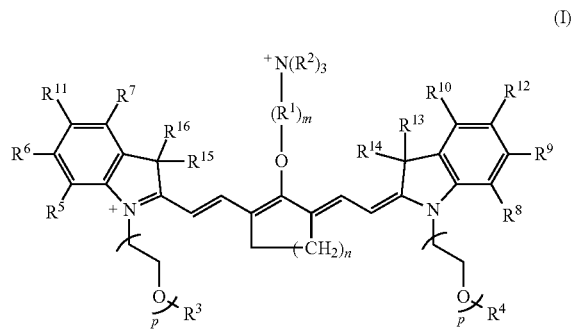

(I)

With respect to Formula I, m is 3, 4, or 5, n is 1, 2, or 3, each p independently is 1, 2, 3, 4, 5, 6, 7, 8, 9, or 10, $R^1$ is —$CR^a{}_2$— where each $R^a$ independently is H, halo, optionally substituted alkyl, or optionally substituted aryl, each $R^2$ independently is methyl, ethyl, n-propyl, or isopropyl, $R^3$ and $R^4$ independently are alkyl, $R^5$ to $R^{10}$ independently are H or alkyl, $R^{11}$ and $R^{12}$ independently are sulfonate, H, or alkyl, and $R^{13}$ to $R^{16}$ independently are alkyl. In some embodiments, the alkyl group is $C_1$-$C_{10}$ alkyl, such as $C_1$-$C_5$ alkyl or $C_1$-$C_3$ alkyl.

In any or all of the above embodiments, the compound according to Formula I may be symmetrical. Thus, in some embodiments, $R^3$ and $R^4$ are the same, $R^5$ and $R^8$ are the same, $R^6$ and $R^9$ are the same, $R^7$ and $R^{10}$ are the same, $R^{11}$ and $R^{12}$ are the same, and $R^{13}$-$R^{16}$ are the same.

In any or all of the above embodiments, $R^1$ may be —$CH_2$—. In any or all of the above embodiments, each $R^2$ may be methyl or ethyl. In any or all of the above embodiments, $R^5$-$R^{10}$ may be H. In any or all of the above embodiments, $R^{11}$ and $R^{12}$ may be sulfonate. In any or all of the above embodiments, $R^{13}$-$R^{16}$ may be alkyl, such as $C_1$-$C_5$ alkyl or $C_1$-$C_3$ alkyl. In any or all of the above embodiments, p may be 1, 2, 3, 4, or 5.

In some embodiments, m is 3. In some embodiments, m is 4. In some embodiments, m is 5. In some embodiments, n is 1. In some embodiments, n is 2. In some embodiments, n is 3. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10.

In some embodiments, $R^a$ is H. In some embodiments, $R^a$ is halo. In some embodiments, $R^a$ is substituted alkyl. In some embodiments, $R^a$ is unsubstituted alkyl. In some embodiments, alkyl is methyl, ethyl, n-propyl, i-propyl, n-butyl, i-butyl, or t-butyl. In some embodiments, $R^a$ is substituted aryl.

In some embodiments, $R^2$ is methyl. In some embodiments, $R^2$ is ethyl. In some embodiments, $R^2$ is n-propyl. In some embodiments, $R^2$ is isopropyl.

In some embodiments, $R^3$ is methyl, ethyl, n-propyl, i-propyl, n-butyl, i-butyl, or t-butyl.

In some embodiments, $R^4$ is methyl, ethyl, n-propyl, i-propyl, n-butyl, i-butyl, or t-butyl.

In some embodiments, $R^5$ is H. In some embodiments, $R^5$ is alkyl. In some embodiments, alkyl is methyl, ethyl, n-propyl, i-propyl, n-butyl, i-butyl, or t-butyl.

In some embodiments, $R^6$ is H. In some embodiments, $R^6$ is alkyl. In some embodiments, alkyl is methyl, ethyl, n-propyl, i-propyl, n-butyl, i-butyl, or t-butyl.

In some embodiments, $R^7$ is H. In some embodiments, $R^7$ is alkyl. In some embodiments, alkyl is methyl, ethyl, n-propyl, i-propyl, n-butyl, i-butyl, or t-butyl.

In some embodiments, $R^8$ is H. In some embodiments, $R^8$ is alkyl. In some embodiments, alkyl is methyl, ethyl, n-propyl, i-propyl, n-butyl, i-butyl, or t-butyl.

In some embodiments, $R^9$ is H. In some embodiments, $R^9$ is alkyl. In some embodiments, alkyl is methyl, ethyl, n-propyl, i-propyl, n-butyl, i-butyl, or t-butyl.

In some embodiments, $R^{10}$ is H. In some embodiments, $R^{10}$ is alkyl. In some embodiments, alkyl is methyl, ethyl, n-propyl, i-propyl, n-butyl, i-butyl, or t-butyl.

In some embodiments, $R^{11}$ is sulfonate. In some embodiments, $R^{11}$ is H. In some embodiments, $R^{11}$ is alkyl. In some embodiments, alkyl is methyl, ethyl, n-propyl, i-propyl, n-butyl, i-butyl, or t-butyl.

In some embodiments, $R^{12}$ is sulfonate. In some embodiments, $R^{12}$ is H. In some embodiments, $R^{12}$ is alkyl. In some embodiments, alkyl is methyl, ethyl, n-propyl, i-propyl, n-butyl, i-butyl, or t-butyl.

In some embodiments, $R^{13}$ is $C_1$-$C_{10}$ alkyl, such as $C_1$-$C_5$ alkyl or $C_1$-$C_3$ alkyl. In some embodiments, $R^{13}$ is methyl, ethyl, n-propyl, i-propyl, n-butyl, i-butyl, or t-butyl.

In some embodiments, $R^{14}$ is $C_1$-$C_{10}$ alkyl, such as $C_1$-$C_5$ alkyl or $C_1$-$C_3$ alkyl. In some embodiments, $R^{14}$ is methyl, ethyl, n-propyl, i-propyl, n-butyl, i-butyl, or t-butyl.

In some embodiments, $R^{15}$ is $C_1$-$C_{10}$ alkyl, such as $C_1$-$C_5$ alkyl or $C_1$-$C_3$ alkyl. In some embodiments, $R^{15}$ is methyl, ethyl, n-propyl, i-propyl, n-butyl, i-butyl, or t-butyl.

In some embodiments, $R^{16}$ is $C_1$-$C_{10}$ alkyl, such as $C_1$-$C_5$ alkyl or $C_1$-$C_3$ alkyl. In some embodiments, $R^{16}$ is methyl, ethyl, n-propyl, i-propyl, n-butyl, i-butyl, or t-butyl.

In any or all of the above embodiments, the compound according to Formula I may be a neutral compound (an overall charge of zero). In any or all of the above embodiments, the compound according to Formula I may have a quantum yield of at least 15%, such as a quantum yield of at least 20%, at least 25%, or at least 30%. In any or all of the above embodiments, the compound according to Formula I may exhibit a maximum emission wavelength within the range of from 700-900 nm. In any or all of the above embodiments, the compound according to Formula I may have a c Log P value of ≤5.0, rendering the compound aqueous soluble. In some embodiments, the compound according to Formula I is unreactive towards thiols (e.g., glutathione) and the cellular proteome.

According to certain embodiments of the present disclosure, the compound has a structure according to Formula IA or a stereoisomer thereof:

(IA)

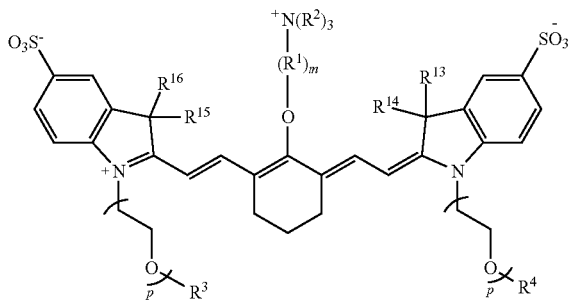

wherein $R^1$ is —$CH_2$—, m is 3 and p is 2, 3, or 4, and $R^2$-$R^4$ and $R^{13}$-$R^{16}$ are as recited above.

In some embodiments, each $R^2$ is methyl. In any or all of the above embodiments, $R^3$ and $R^4$ may be methyl. In any or all of the above embodiments, $R^{13}$-$R^{16}$ may be methyl.

In one embodiment, the compound according to Formula I is:

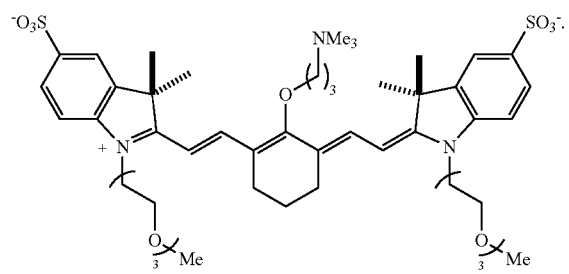

According to certain embodiments of the present disclosure, a heptamethine cyanine compound has a structure according to Formula II or a stereoisomer or tautomer thereof:

(II)

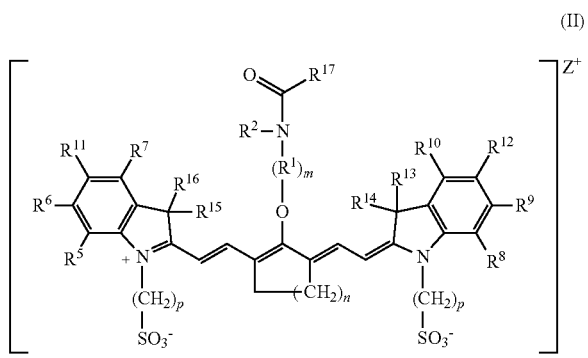

With respect to Formula II, m is 2, 3, 4, or 5, n is 1, 2, or 3, each p independently is 1, 2, 3, 4, 5, 6, 7, 8, 9, or 10, $R^1$ is —$CR^a_2$— where each $R^a$ independently is H, halo, optionally substituted alkyl, or optionally substituted aryl, $R^2$ is $C_1$-$C_3$ alkyl, $R^5$ to $R^{12}$ independently are H or alkyl, $R^{13}$ to $R^{16}$ independently are alkyl, $R^{17}$ is $C_1$-$C_3$ alkyl, and Z is a monatomic ion. In some embodiments, the alkyl group is $C_1$-$C_{10}$ alkyl, such as $C_1$-$C_5$ alkyl or $C_1$-$C_3$ alkyl.

In any or all of the above embodiments, the compound according to Formula II may be symmetrical. Thus, in some embodiments, $R^5$ and $R^8$ are the same, $R^6$ and $R^9$ are the same, $R^7$ and $R^{10}$ are the same, $R^{11}$ and $R^{12}$ are the same, and $R^{13}$-$R^{16}$ are the same.

In any or all of the above embodiments, $R^1$ may be —$CH_2$—. In any or all of the above embodiments, $R^2$ may be methyl or ethyl. In any or all of the above embodiments, $R^5$-$R^{12}$ may be H. In any or all of the above embodiments, $R^{13}$-$R^{16}$ may be alkyl, such as $C_1$-$C_5$ alkyl or $C_1$-$C_3$ alkyl. In some embodiments, $R^{13}$-$R^{16}$ are methyl. In any or all of the above embodiments, p may be 2, 3, 4, 5, or 6. In any or all of the above embodiments, $Z^+$ may be $Na^+$ or $K^+$.

In some embodiments, m is 2. In some embodiments, m is 3. In some embodiments, m is 4. In some embodiments, m is 5. In some embodiments, n is 1. In some embodiments, n is 2. In some embodiments, n is 3. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10.

In some embodiments, $R^a$ is H. In some embodiments, $R^a$ is halo. In some embodiments, $R^a$ is substituted alkyl. In some embodiments, $R^a$ is unsubstituted alkyl. In some embodiments, alkyl is methyl, ethyl, n-propyl, i-propyl, n-butyl, i-butyl, or t-butyl. In some embodiments, $R^a$ is substituted aryl.

In some embodiments, $R^2$ is $C_1$-$C_3$ alkyl.

In some embodiments, $R^5$ is H. In some embodiments, $R^5$ is alkyl. In some embodiments, alkyl is methyl, ethyl, n-propyl, i-propyl, n-butyl, i-butyl, or t-butyl.

In some embodiments, $R^6$ is H. In some embodiments, $R^6$ is alkyl. In some embodiments, alkyl is methyl, ethyl, n-propyl, i-propyl, n-butyl, i-butyl, or t-butyl.

In some embodiments, $R^7$ is H. In some embodiments, $R^7$ is alkyl. In some embodiments, alkyl is methyl, ethyl, n-propyl, i-propyl, n-butyl, i-butyl, or t-butyl.

In some embodiments, $R^8$ is H. In some embodiments, $R^8$ is alkyl. In some embodiments, alkyl is methyl, ethyl, n-propyl, i-propyl, n-butyl, i-butyl, or t-butyl.

In some embodiments, $R^9$ is H. In some embodiments, $R^9$ is alkyl. In some embodiments, alkyl is methyl, ethyl, n-propyl, i-propyl, n-butyl, i-butyl, or t-butyl.

In some embodiments, $R^{10}$ is H. In some embodiments, $R^{10}$ is alkyl. In some embodiments, alkyl is methyl, ethyl, n-propyl, i-propyl, n-butyl, i-butyl, or t-butyl.

In some embodiments, $R^{11}$ is H. In some embodiments, $R^{11}$ is alkyl. In some embodiments, alkyl is methyl, ethyl, n-propyl, i-propyl, n-butyl, i-butyl, or t-butyl.

In some embodiments, $R^{12}$ is H. In some embodiments, $R^{12}$ is alkyl. In some embodiments, alkyl is methyl, ethyl, n-propyl, i-propyl, n-butyl, i-butyl, or t-butyl.

In some embodiments, $R^{13}$ is alkyl. In some embodiments, the alkyl group is $C_1$-$C_{10}$ alkyl, such as $C_1$-$C_5$ alkyl or $C_1$-$C_3$ alkyl.

In some embodiments, $R^{14}$ is alkyl. In some embodiments, the alkyl group is $C_1$-$C_{10}$ alkyl, such as $C_1$-$C_5$ alkyl or $C_1$-$C_3$ alkyl.

In some embodiments, $R^{15}$ is alkyl. In some embodiments, the alkyl group is $C_1$-$C_{10}$ alkyl, such as $C_1$-$C_5$ alkyl or $C_1$-$C_3$ alkyl.

In some embodiments, $R^{16}$ is alkyl. In some embodiments, the alkyl group is $C_1$-$C_{10}$ alkyl, such as $C_1$-$C_5$ alkyl or $C_1$-$C_3$ alkyl.

In some embodiments, $R^{17}$ is $C_1$-$C_3$ alkyl.

In some embodiments, Z is a monatomic ion.

In any or all of the above embodiments, the compound according to Formula II may have a quantum yield of at least 15%, such as a quantum yield of at least 20% or at least 25%. In any or all of the above embodiments, the compound according to Formula II may exhibit a maximum emission wavelength within the range of from 700-900 nm. In any or all of the above embodiments, the compound according to Formula II may have a c Log P value of ≤5.0, rendering the compound aqueous soluble. In some embodiments, the compound according to Formula II is unreactive towards thiols (e.g., glutathione) and the cellular proteome.

According to certain embodiments of the present disclosure, the heptamethine cyanine has a structure according to Formula IIA, or a stereoisomer or tautomer thereof:

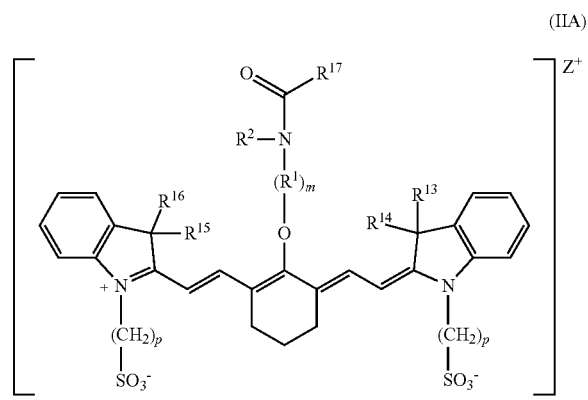

(IIA)

wherein $R^1$ is —$CH_2$—, m is 2, and p is 3, 4, or 5.

In any or all of the above embodiments, $R^2$ may be methyl. In any or all of the above embodiments, $R^{13}$ to $R^{16}$ may be methyl. In any or all of the above embodiments, $R^{17}$ may be methyl or ethyl.

In one embodiment, the compound according to Formula II is:

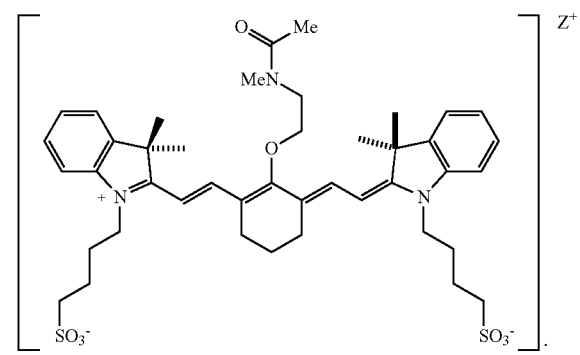

III. Pharmaceutical Compositions

According to an embodiment, the present disclosure includes pharmaceutical compositions comprising at least one heptamethine cyanine as disclosed herein. Some embodiments of the pharmaceutical compositions include a pharmaceutically acceptable carrier and at least one heptamethine cyanine. Useful pharmaceutically acceptable carriers and excipients are known in the art.

The pharmaceutical compositions comprising one or more heptamethine cyanines may be formulated in a variety of ways based, for example, on the mode of administration and/or on the location to be imaged. Parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as Cremophor® polyethoxylated castor oil, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The form of the pharmaceutical composition can be determined by the mode of administration chosen. Embodiments of the disclosed pharmaceutical compositions may take a form suitable for virtually any mode of administration, including, for example, oral, buccal, systemic, injection, transdermal, rectal, etc., or a form suitable for administration by inhalation or insufflation. Generally, embodiments of the disclosed pharmaceutical compositions will be administered by injection, systemically, or orally.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspensions, solutions or emulsions in oily or aqueous vehicles, and may contain formulatory agents such as suspending, stabilizing and/or dispersing agents. For example, parenteral administration may be done by bolus injection or continuous infusion. Alternatively, the heptamethine cyanine may be in powder form for reconstitution with a suitable vehicle, e.g. sterile water, before use.

Systemic formulations include those designed for administration by injection, e.g., subcutaneous, intravenous, intramuscular, or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some heptamethine cyanine formulations may be dried, e.g., by spray-drying with a disaccharide, to form heptamethine cyanine powders. Solid compositions prepared by conventional means with pharmaceutically acceptable excipients such as binding agents (e.g., pregelatinised maize starch, polyvinylpyrrolidone or hydroxypropyl methylcellulose), fillers (e.g., lactose, mannitol, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol, Cremophor® or fractionated vegetable oils), and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the fluorophore, as is well known.

For rectal administration, the heptamethine cyanine(s) may be formulated as solutions (for retention enemas), suppositories, or ointments containing conventional suppository bases such as cocoa butter or other glycerides. For nasal administration or administration by inhalation or insufflation, the heptamethine cyanine(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

According to certain embodiments the present disclosure, pharmaceutical compositions comprising heptamethine cyanines as described herein may be formulated in unit dosage form suitable for individual administration of precise dosages. The pharmaceutical compositions may, if desired, be presented in a pack or dispenser device which may contain one or more unit dosage forms containing the heptamethine cyanine. The pack may, for example, comprise metal or plastic foil, such as a blister pack. The pack or dispenser device may be accompanied by instructions for administration.

The amount of heptamethine cyanine administered will depend at least in part on the subject being treated, the target (e.g., the biliary system or the renal system), and the manner of administration, and may be determined as is known to those skilled in the art of pharmaceutical composition and/or contrast agent administration. Within these bounds, the formulation to be administered may contain a quantity of the heptamethine cyanine disclosed herein in an amount effective to enable visualization of the heptamethine cyanine by suitable means after administration to the subject. In some embodiments an effective amount of the heptamethine cyanine is from 1 µg/kg body weight to 240 µg/kg, such as 10-240 µg/kg, 20-240 µg/kg, 40-240 µg/kg, 50-200 µg/kg, or 50-150 µg/kg.

IV. Synthesis

According to an certain embodiments of the present disclosure, disclosed herein are methods for making heptamethine cyanine compounds according to Formula I or Formula II.

An exemplary synthesis for making heptamethine cyanines according to Formula I is shown in FIG. 1. An indolenine 1 is combined with an alkyl or heteroalkyl iodide under conditions effective to alkylate the nitrogen. In the scheme of FIG. 1, the indolenine 1 is alkylated with 1-iodo-2-(2-(2-methoxyethoxy)ethoxy)ethane ($H_3C(OCH_2CH_2)_3I$) in methyl cyanide at 120° C. to provide compound 3. A cyanine is formed by reaction of compound 3 with compound 4 (N-[(3-(anilinomethylene)-2-chloro-1-cyclohexen-1-yl)methylene]aniline monohydrochloride), e.g., in refluxing ethanol with triethylamine and acetic anhydride to produce compound 5. Compound 5 may be purified by reversed-phase purification. The C4' chloro substituent is replaced by reaction with an alkanolamine. For example, the ethyl congener (compound 6) is made by reaction of compound 5 with N-methylethanolamine, e.g., by addition of N-methylethanolamine in N,N'-dimethylformamide (DMF) at 75° C. A Smiles-type rearrangement of compound 6 is effected by reaction with a compound capable of initiating an N- to O-rearrangement, e.g., an alkyl halide. In FIG. 1, the rearrangement of compound 6 proceeds using methyl iodide and sodium bicarbonate in DMF at 95° C. to provide compound 8.

To prepare a propyl variant (compound 7), compound 5 is reacted with N-methylpropanolamine in DMF at 75° C. Rearrangement of compound 7 to provide compound 9 is a two-step process. In a first step, compound 7 is reacted with trifluoroacetic acid (TFA) and the solvent is then removed. TFA treatment of compound 7 induces an —N to —O transposition (based on a bathochromic shift in the absorbance maxima). The intermediate then undergoes N-alkylation by heating with methyl iodide in DMF at 60° C. to provide compound 9.

Figure 2:
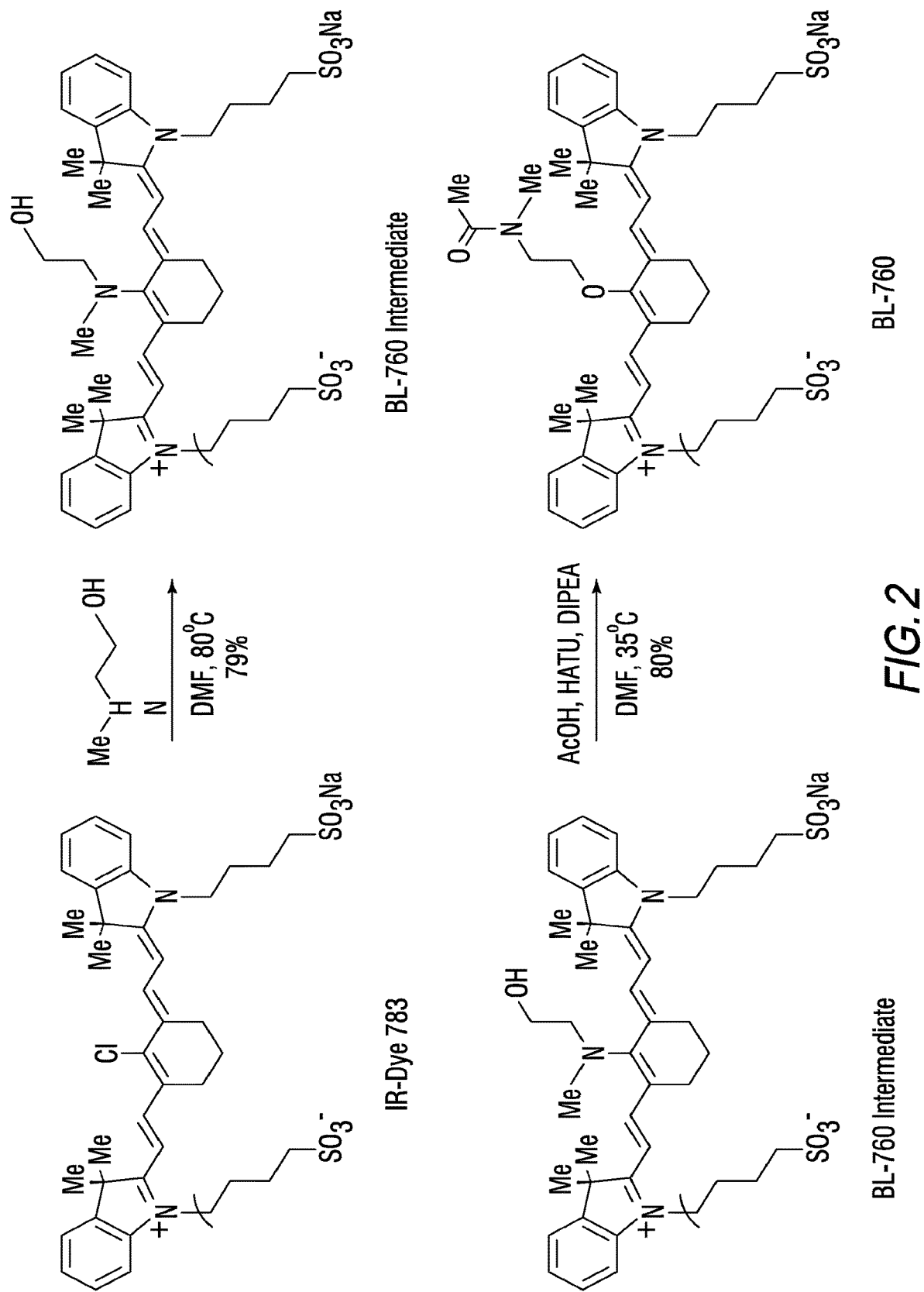
FIG. 2 is an exemplary synthesis scheme for making some embodiments of the disclosed heptamethine cyanine compounds according to Formula II.

An exemplary synthesis for making heptamethine cyanines according to Formula II is shown in FIG. 2. A commercially available dye, IR-Dye 783, is combined with an alkanolamine under conditions effective to replace the C4'-chloro substituent with the alkanolamine. In the scheme of FIG. 2, IR-Dye 783 is combined with 2-(methylamino)ethanol) in DMF at 80° C. to provide an intermediate compound, BL-760 intermediate. The intermediate may be purified by reversed phase chromatography. A rearrangement and acylation of the BL-760 intermediate is effected by reaction with a compound capable of initiating an N- to O-rearrangement and an acylation catalyst. In FIG. 2, rearrangement and acylation proceeds by combining acetic acid, HATU (1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-yl-methylene]-N-methylmethanaminium hexafluorophosphate N-oxide), and DIPEA (N,N-diisopropylethylamine) in DMF to provide an activated ester solution. The BL-760 intermediate is combined with the activated ester solution and heated to 35° C. overnight to provide the BL-760 compound. BL-760 may be purified by reversed phase chromatography.

V. Methods of Use

According to certain embodiments, the disclosed heptamethine cyanines may be useful for live-cell visualization and tracking applications. Further, investigative and diagnostic uses are within the scope of the disclosure.

According to certain embodiments, the disclosed heptamethine cyanines are utilized for in vivo visualization and tracking applications. For example, certain embodiments of the disclosed compounds are useful for visualizing at least a portion of a renal system or a biliary system of a subject.

Figure 3:
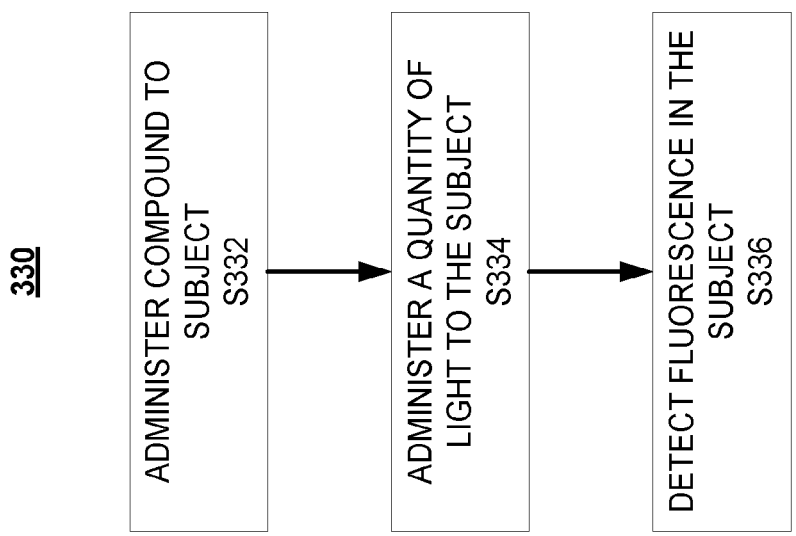
FIG. 3 is a high-level flow diagram of a method for using the disclosed heptamethine cyanine compounds by injection of the compound into a subject followed by targeted delivery of light of a desired wavelength to the at least a portion of the subject's biliary and/or renal system.

A method for visualizing at least a portion of a renal system or a biliary system of a subject is described in FIG. 3. With reference to FIG. 3, the method can be a process 330 and can include, at step 332 of process 330, administering to the subject a compound as disclosed herein or

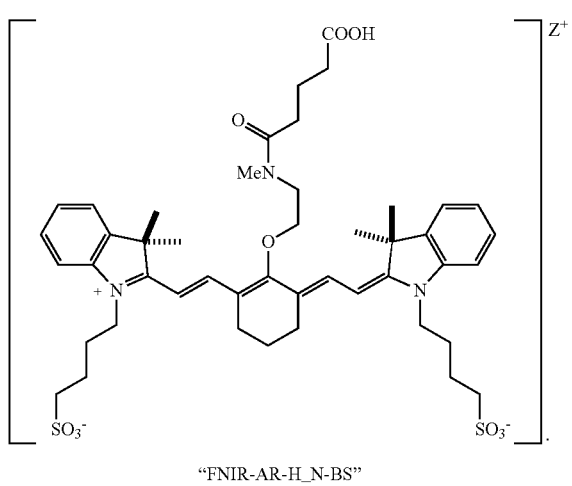

"FNIR-AR-H_N-BS"

wherein Z is a monatomic ion. At step 334 of process 330, a quantity of light can be delivered to a targeted portion of the subject, wherein the quantity of light has a wavelength and intensity sufficient to produce fluorescence of the compound. At step 336 of process 330, fluorescence in the targeted portion of the subject can be detected, fluorescence indicating the presence of the compound in the targeted portion of the subject. In some embodiments, the administered compound is a compound according to Formula IA, Formula IIA, or compound FNIR-Ar-H_N-BS.

Administering the compound to the subject may comprise administering an effective amount of the compound such that fluorescence is detectable if the compound is present in the targeted portion of the subject. In some embodiments, administering the compound comprises administering a pharmaceutical composition comprising the compound and a pharmaceutically acceptable carrier. In any or all of the above embodiments, the light may have a wavelength or a range of wavelengths in the near-infrared range.

In some embodiments, visualization comprises irradiating the sample or a targeted portion of a subject with targeted application of a quantity of light having a wavelength in the visible, far-red, or near-infrared range and a selected intensity, wherein the quantity of light is sufficient to produce fluorescence of the compound, and detecting any fluorescence emitted by the compound. Advantageously, the light has a wavelength at or near a maximum absorption wavelength of the heptamethine cyanine. For example, the sample may be irradiated with light having a wavelength within a range of 650 nm to 2500 nm, such as from 650-900 nm, or 750-850 nm. In some embodiments, the light source is a laser, LED (light-emitting diode), xenon lamp, halogen bulb, VSCEL (vertical-cavity surface-emitting laser), or others. Suitable light intensities may range from 1 mW/cm$^2$ to 1000 mW/cm$^2$, such as 1-750 mW/cm$^2$ or 300-700 mW/cm$^2$, depending on the target site and method of application. Near-infrared light sources can be obtained from commercial sources, including Thorlabs (Newton, N.J.), Laser Components, USA (Hudson, N.H.), ProPhotonix (Salem, N.H.) and others. In some embodiments, the effective quantity of NIR light is 0.1-1000 mW/cm$^2$, such as 0.1-300 mW/cm$^2$.

In some embodiments, an effective amount of a heptamethine cyanine or a pharmaceutical composition comprising the compound is administered to a subject suspected of having a condition that may be detected and/or evaluated by visualizing the subject's biliary and/or renal system. Administration is performed by any suitable method, e.g., intravenous, intra-arterial, intramuscular, intratumoral, or subcutaneous injection, or oral, intranasal, or sublingual administration. The administered compound is subsequently irradiated by targeted application of a quantity of light having a wavelength in the near-infrared range and a selected intensity to a target area of the subject, wherein the quantity of light is sufficient to excite the heptamethine cyanine. When irradiating a target area (e.g., a portion of the biliary system or renal system), the effective quantity of NIR light may be 0.1-1000 mW/cm$^2$, such as 0.1-300 mW/cm$^2$. Any fluorescence from the compound in the targeted portion of the subject is detected, thereby diagnosing the subject as having the condition.

The surface area for light application is generally selected to include target tissue, e.g., the biliary and/or renal system or a portion thereof, or an area of skin external to the target tissue. When targeted application of external light is desired for an in vivo biological sample, the surface area can be controlled by use of an appropriate light applicator, such as a micro-lens, a Fresnel lens, or a diffuser arrangement. For targeted internal light application, a desired endoscope or fiber optic catheter diameter can be selected. In some applications, an indwelling catheter filled with a light scattering solution may be internally placed proximate the target tissue, and an optical fiber light source may be inserted into the catheter (see, e.g., Madsen et al., *Lasers in Surgery and Medicine* 2001, 29, 406-412).

Figure 4:
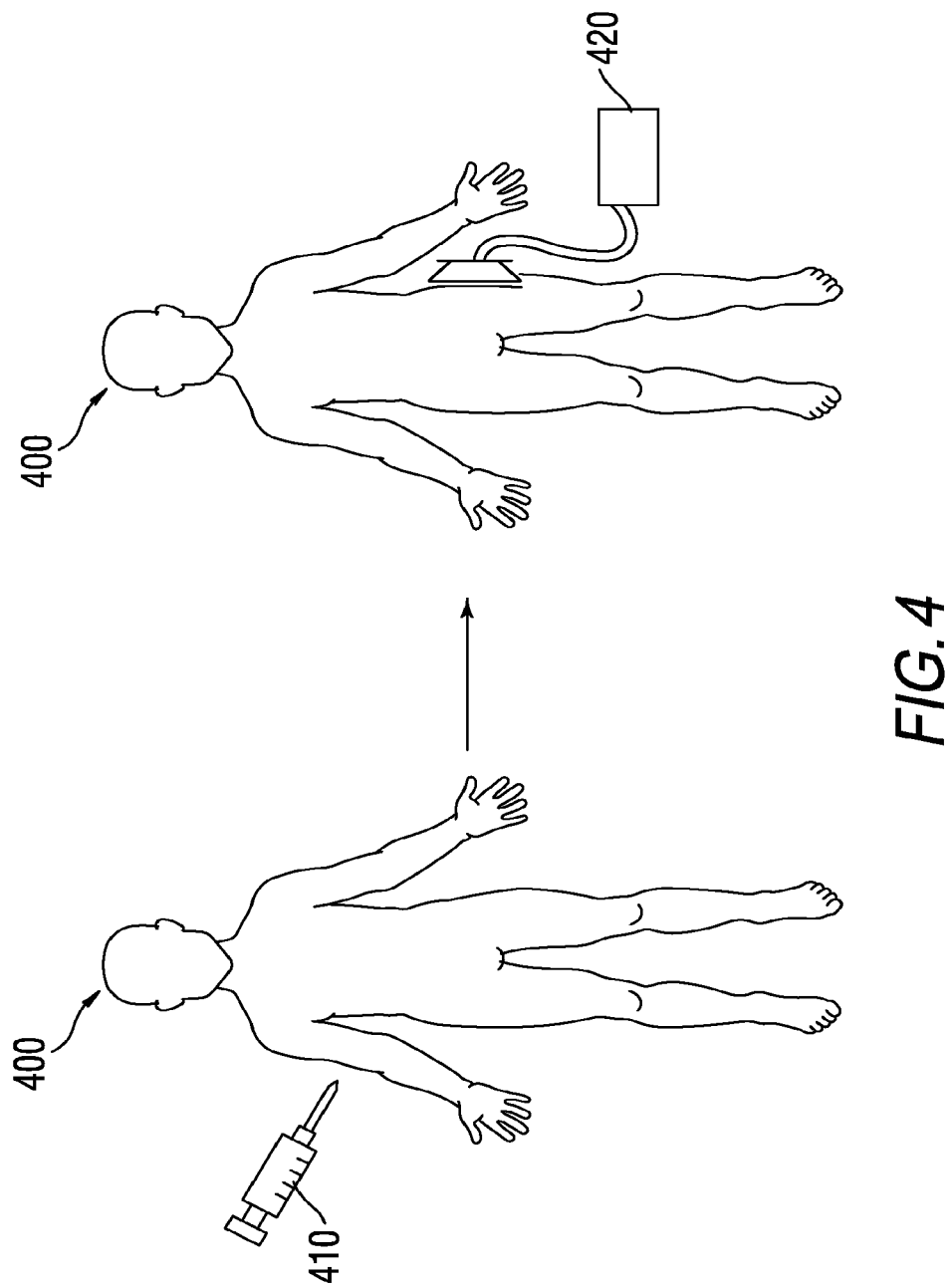
FIG. 4 is a schematic diagram illustrating one embodiment of a method for using the disclosed heptamethine cyanine compounds by injection of the compound into a subject followed by targeted delivery of light of a desired wavelength to the at least a portion of the subject's biliary and/or renal system.

For example, in view of FIG. 3 and with reference to FIG. 4, a subject 400, or patient, may be administered a heptamethine cyanine compound 410, e.g., via intravenous injection. A period of time is allowed to elapse during which the compound preferentially accumulates in the biliary and/or renal system. A target portion of the subject subsequently is selectively irradiated with an effective amount of NIR light energy of a desired wavelength using an external light applicator 420. The light applicator 420 applies the light to a target area, wherein the target area comprises at least a portion of the biliary or renal system, thereby producing fluorescence of the compound. The portion of the biliary or renal system is visualized by detecting the fluorescence.

According to an embodiment of the present disclosure, the targeted portion of the subject may be at least a portion of the renal system and the heptamethine cyanine is a compound according to Formula I or Formula IA. In an embodiment, the light may have a wavelength within a range of from 600-850 nm. In an embodiment, the compound may be compound 9 (also referred to as UL-766):

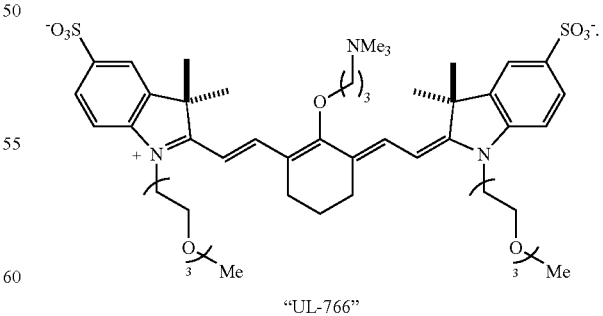

"UL-766"

This is important as the ureter is vulnerable to external trauma and iatrogenic injuries during various surgical procedures, including open surgery, laparoscopy, and endoscopic procedures. Nearly any abdominopelvic surgical procedure, whether gynecologic, obstetric, general surgical, or urologic can potentially injure the ureter. The incidence of ureter injury during abdominal and pelvic surgery has been reported to range from 0.5% to 10% (Gioux et al., *Mol Imaging* 2010, 9(5):237-255; Reinhart et al., *Surgical Innovation* 2015; Verbeek et al., *J Urology* 2013, 190(2):574-579). This injury rate is largely attributed to the close position of the ureter to vascular structures, combined with their course along virtually every level of the retroperitoneum and upper pelvis. The visualization of the ureter without inserting additional stents or evoking peristalsis by touching instruments is beneficial for evaluating acute ureteral injuries. Ureteral leakage can also be instantaneously examined after ureteral anastomosis is performed. Importantly, clear visualization during surgery through fluorescence-guided surgical methods could alleviate this significant morbidity.

Advantageously, certain compounds according to Formula I or Formula IA, such as UL-766, undergo excellent renal clearance and can be used to display the ureter using a NIR fluorescence imaging system. UL-766 exhibits improved specificity for renal clearance compared to the commercially available IR-800CW compound dye. Moreover, this compound exhibits reduced reactivity with biological nucleophiles. The reduced reactivity of UL-766 and related molecules may be important from a clinical toxicology perspective.

Some heptamethine cyanine compounds according to Formula I or Formula IA can be injected intravenously into a subject at a low dose (e.g., 1-100 µg/kg body weight), and are sensitive enough to be visualized quickly after injection as well as over an extended period of time. In some embodiments, the heptamethine cyanine produces a contrast-to-background ratio (CBR) of at least 1.5, at least 2.0, at least 2.5, at least 3, or at least 4 within minutes of injection, such as within 20 minutes, within 15 minutes, within 10 minutes, or within 5 minutes. In certain embodiments, the heptamethine cyanine produces a CBR of from 2-10, such as from 3-5 within 10 minutes following intravenous injection into the subject. In some embodiments, a CBR ratio of at least 1.5 is maintained for at least 30 minutes, at least 45 minutes, or at least 60 minutes after injection, such as for a timeframe of from 10-30 minutes, 10-45 minutes, 10-60 minutes, 5-60 minutes, or 5-90 minutes post-injection. Some embodiments of heptamethine cyanines according to Formula I or Formula IA have a quantum yield of at least 15%, such as a quantum yield of at least 20%, at least 25%, or at least 30%. Advantageously, fluorescence is specific to the renal system. For example, when considering fluorescence in the biliary and renal systems, at least 85%, at least 90%, or at least 95% of the visualized fluorescence may be in the renal system. UL-766, for example, exhibits a biliary:urinary specificity of 5:95 with a quantum yield of 30%.

According to an embodiment of the present disclosure, the targeted portion of the subject comprises at least a portion of the biliary system, and the heptamethine cyanine can be a compound according to Formula II, Formula IIA, or

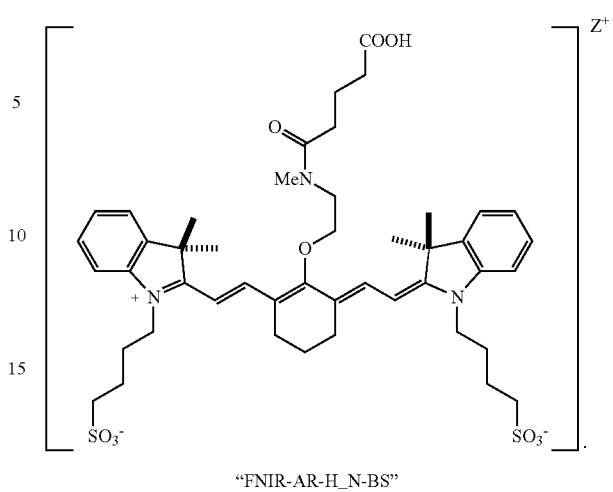

"FNIR-AR-H_N-BS"

In certain embodiments, the light has a wavelength within a range of from 600 nm to 850 nm.

According to an embodiment, in certain examples, the compound can be

"BL-760"

Advantageously, certain compounds according to Formula II, or Formula IIA, such as BL-760, and FNIR-Ar-H_N-BS undergo excellent biliary clearance and can be used to display the biliary system or a portion thereof using a NIR fluorescence imaging system. Compared to commercially available dyes, such as indocyanine green (ICG) and the IRDye® 800CW compound, some compounds according to Formula II, Formula IIA, or FNIR-Ar-H_N-BS exhibit greater biliary:urinary specificity, faster excretion into bile, and/or greater quantum yield.

According to an embodiment, some heptamethine cyanine compounds according to Formula II, Formula IIA, or FNIR-Ar-H_N-BS can be injected intravenously into a subject at a low dose, excrete quickly into bile, and are sensitive enough to visualize quickly after injection. In some embodiments, an amount of the heptamethine cyanine compound sufficient to enable visualization is excreted into bile within 5 minutes following intravenous injection of a minimum threshold amount (e.g., 1-100 µg/kg body weight) of the compound into the subject. Some embodiments of heptamethine cyanines according to Formula II, Formula IIA, or FNIR-Ar-H_N-BS have a quantum yield of at least 15%, such as a quantum yield of at least 20% or at least 25%.

Advantageously, when considering fluorescence in the biliary and renal systems, at least 85%, at least 90%, at least 95%, or 100% of the visualized fluorescence may be in the biliary system. For example, FNIR-Ar-H_N-BS has a biliary:urinary specificity of 95:5 and BL-760 has a biliary: urinary specificity of 100:0.

Figure 5:
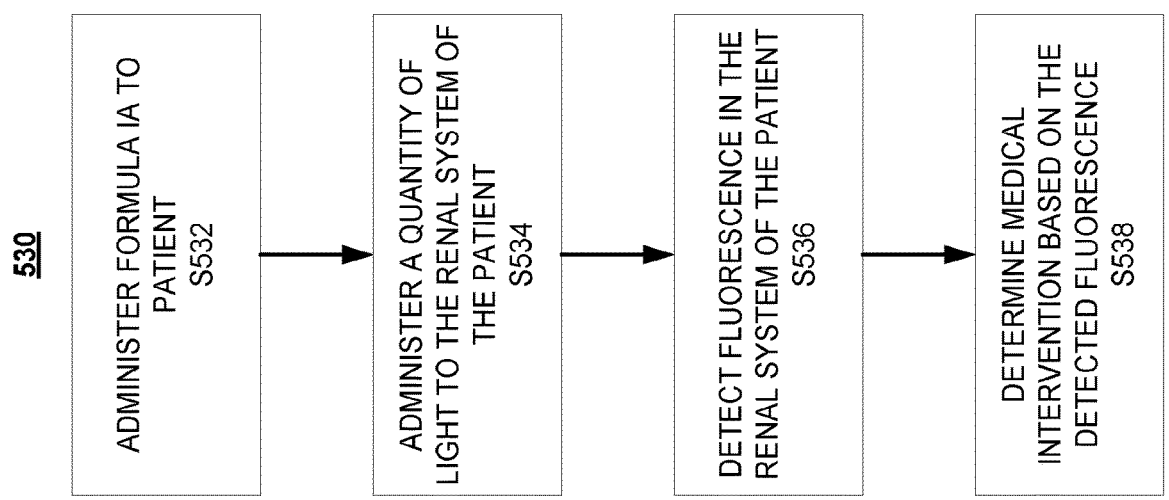
FIG. 5 is a low-level flow diagram of a method of using the disclosed heptamethine cyanine compounds for evaluation of a renal system of a patient, according to an exemplary embodiment of the present disclosure.

According to an embodiment, the present disclosure is related to a method for visualization at least a portion of a renal system of a patient. Ureters are often difficult to identify and at risk for injury, especially in settings of inflammation and distorted anatomy. Current aids of identification are not always effective. The use of fluorescent dye can improve intraoperative ureteral identification without the need for any additional, invasive procedures. Moreover, improved intraoperative identification of ureteral structures minimizes risks of iatrogenic injury to the ureters, especially in cases of abdominal surgery to adjacent tissues. In view of the above, according to an embodiment, the method for visualization of at least the portion of the renal system of the patient can be a method for visualization of an ureteropelvic junction and surrounding tissues, providing insight, for instance, as to any blockages of a ureter or any iatrogenic injuries sustained during abdominal surgery. With reference to FIG. 5, the method can be a process 530. At step 532 of process 530, a compound can be administered to a subject. In context of the ureteropelvic junction of the renal system, the compound can be Formula IA, or UL-766, and the subject can be a patient. At step 534 of process 530, a quantity of light can be administered to the ureteropelvic junction of the patient, wherein the quantity of light has a wavelength and intensity sufficient to produce fluorescence of UL-766. It can be appreciated that the quantity of light can be administered after a period of time to allow UL-766 to reach the renal system. At step 536 of process 530, fluorescence of UL-766 in the ureteropelvic junction of the renal system, in response to the administration of the quantity of light, can be detected. In an embodiment and based on the surgical plan, an evaluation can be made based on the detected fluorescence. If, in an example, detected fluorescence is accumulated in the renal pelvis, it can be determined that the ureter is obstructed. If, in an example, detected fluorescence is leaking into the abdominal cavity, it can be determined that an iatrogenic injury has occurred and the renal system has been incised. Either determination would necessitate additional action.

Figure 6:
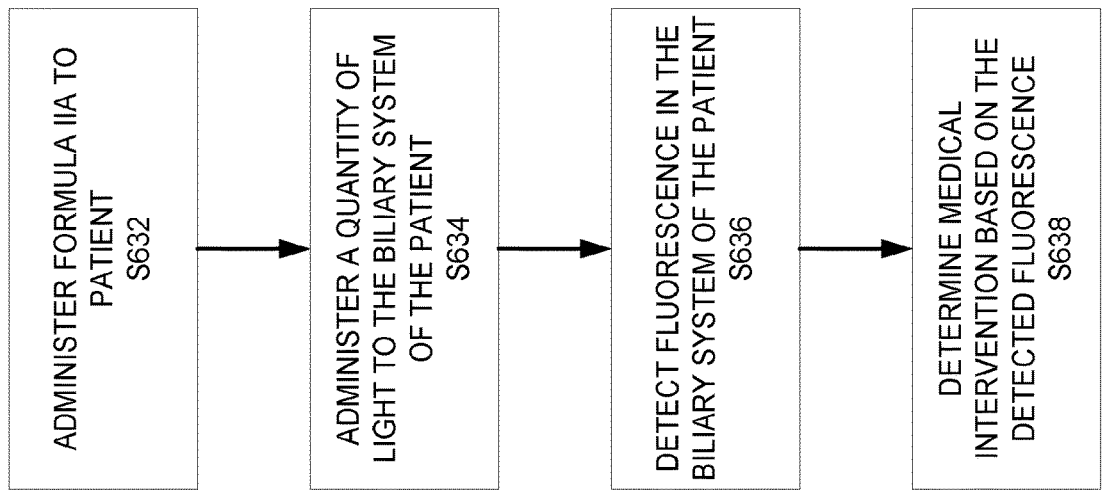
FIG. 6 is a low-level flow diagram of a method of using the disclosed heptamethine cyanine compounds for evaluation of a biliary system of a patient, according to an exemplary embodiment of the present disclosure.

According to an embodiment, the present disclosure is further related to a method for visualization at least a portion of a biliary system of a patient. Visual inspection, palpation, and intraoperative ultrasound remain the most utilized tools during surgery today in the identification of biliary structures during hepatobiliary surgery. These methods are problematic, however, especially in minimally invasive or robot-assisted surgery where palpation is not possible. In these cases, the risk of iatrogenic injury to hepatic tissue, the biliary tree, etc., during such surgeries is increased. In view of the above, according to an embodiment, the method for visualization of at least the portion of the biliary system of the patient can be a method for visualization of a biliary tree and surrounding tissues, providing insight, for instance, as to any iatrogenic injuries to the biliary tree during hepatobiliary surgery. With reference to FIG. 6, the method can be a process 630. At step 632 of process 630, a compound can be administered to a subject. In context of the biliary tree of the biliary system, the compound can be Formula TIA, or BL-760, and the subject can be a patient. At step 634 of process 630, a quantity of light can be administered to the biliary tree of the patient, wherein the quantity of light has a wavelength and intensity sufficient to produce fluorescence of BL-760. It can be appreciated that the quantity of light can be administered after a period of time to allow BL-760 to reach the biliary system. At step 736 of process 730, fluorescence of BL-760 in the biliary tree of the biliary system, in response to the administration of the quantity of light, can be detected. In an embodiment and based on the surgical plan, an evaluation can be made based on the detected fluorescence. If, in an example, bile leakage is indicated by detected fluorescence leaking into the abdominal cavity, it can be determined that an iatrogenic injury has occurred and the biliary tree has been incised. Such determination would necessitate additional action.

Figure 7:
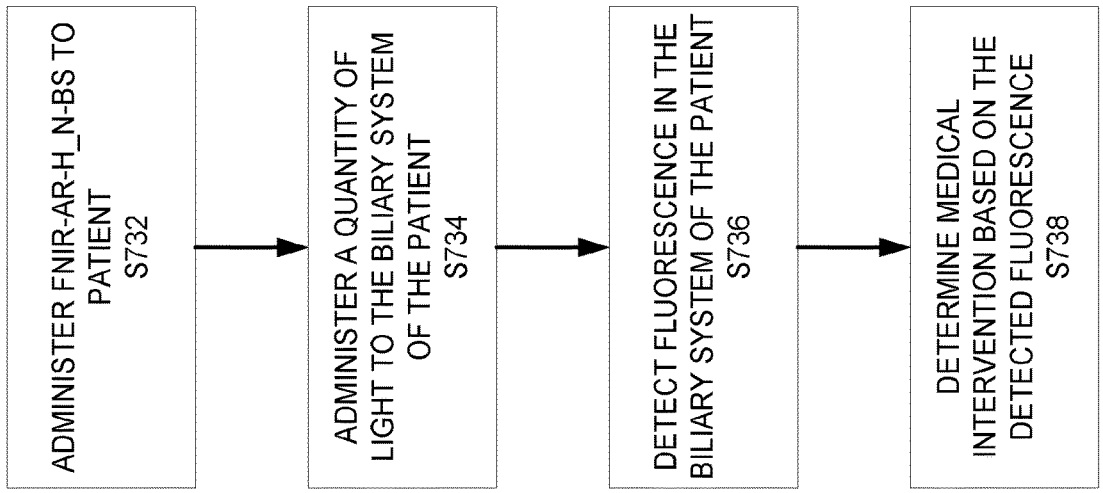
FIG. 7 is a low-level flow diagram of a method of using the disclosed heptamethine cyanine compounds for evaluation of a biliary system of a patient, according to an exemplary embodiment of the present disclosure.

According to an embodiment, the present disclosure is further related to a method for visualization at least a portion of a hepatobiliary system of a patient. Specifically, the method for visualization of at least the portion of the hepatobiliary system of the patient can be a method for visualization of a bile duct, providing insight, for instance, as to any iatrogenic injuries to the bile duct during hepatobiliary surgery. With reference to FIG. 7, the method can be a process 730. At step 732 of process 730, a compound can be administered to a subject. In context of the bile duct of the hepatobiliary system, the compound can be FNIR-AR-H_N-BS and the subject can be a patient. At step 734 of process 730, a quantity of light can be administered to the bile duct of the patient, wherein the quantity of light has a wavelength and intensity sufficient to produce fluorescence of FNIR-AR-H_N-BS. It can be appreciated that the quantity of light can be administered after a period of time to allow FNIR-AR-H_N-BS to reach the bile duct. At step 736 of process 730, fluorescence of FNIR-AR-H_N-BS in the bile duct of the hepatobiliary system, in response to the administration of the quantity of light, can be detected. In an embodiment and based on the surgical plan, an evaluation can be made based on the detected fluorescence. If, in an example, detected fluorescence is leaking into the abdominal cavity, it can be determined that an iatrogenic injury has occurred and the bile duct has been incised. Such determination would necessitate additional action.

According to an embodiment, the present disclosure is further related to the detection of cancer.

Specifically, according to an embodiment, the present disclosure is further related to a method for visualizing at least a portion of a hepatic tissue of a patient, including administering Formula IIA or FNIR-AR-H_N-BS, subsequently administering a quantity of light to the hepatic tissue of the patient, wherein the quantity of light has a wavelength and an intensity sufficient to produce fluorescence of Formula IIA or FNIR-AR-H_N-BS, detecting fluorescence in the hepatic tissue of the patient, and determining, based on the detecting fluorescence in the hepatic tissue of the patient, hepatocellular carcinoma in the hepatic tissue of the patient.

According to an embodiment, the present disclosure is further related to a method for visualizing at least a portion of a hepatic tissue of a patient, including administering Formula IIA or FNIR-AR-H_N-BS, subsequently administering a quantity of light to the hepatic tissue of the patient, wherein the quantity of light has a wavelength and an intensity sufficient to produce fluorescence of Formula IIA or FNIR-AR-H_N-BS, detecting fluorescence in the hepatic tissue of the patient, and determining, based on the detecting fluorescence in the hepatic tissue of the patient, colorectal liver metastasis in the hepatic tissue of the patient.

VI. Kits

According to an embodiment, the present disclosure further describes kits. Embodiments of the kits include at least one heptamethine cyanine compound according to Formula I or Formula II. In some embodiments, the kits also include at least one solution in which the compound may be dissolved or suspended. The kits may also include one or more containers, such as a disposable vial or syringe. The kits may further include instructions for using the compound.

In an embodiment of the kits, the heptamethine cyanine can be provided as a solid, and the solution can be provided in liquid form. The solution may be a solution suitable for dissolving the heptamethine cyanine so that the dissolved compound may be administered to a subject. The solution may be provided at a concentration suitable for the intended use, e.g., intravenous injection. Alternatively, the solution may be provided as a concentrated solution, which is subsequently diluted prior to use.

In an embodiment of the kits, the heptamethine cyanine can be provided as a pharmaceutical composition, e.g., a pharmaceutical composition suitable for intravenous injection. In certain embodiments, the pharmaceutical composition may be premeasured into one or more containers (e.g., vials or syringes).

VII. Non-Limiting Examples

VII.i. Compound Synthesis

Generally, unless stated otherwise, reactions were conducted in oven-dried glassware under an atmosphere of nitrogen or argon using anhydrous solvents (passed through activated alumina columns). All commercially obtained reagents were used as received. N-[(3-(anilinomethylene)-2-chloro-1-cyclohexen-1-yl)methylene]aniline monohydrochloride was purchased from Sigma-Aldrich (St. Louis, Mo.). IR-800CW compound was purchased from Li-Cor Biosciences (Lincoln, Nebr.).

VII.i.a. UL-766.

To a microwave vial equipped with a magnetic stir bar was added indolenine 1 (3.0 g, 10.8 mmol; Park et al., *Bioconjugate Chem.* 2012, 23:350), MeCN (12 mL) and iodide 2 (3.0 g, 10.8 mmol; Lawal et al., *Supramol. Chem.* 2009, 21:55). The vessel was sealed under argon and the light brown slurry was heated to 120° C. in a sand bath for 22 hours during which time the reaction changed to a deep red/pink color. The reaction was cooled and the

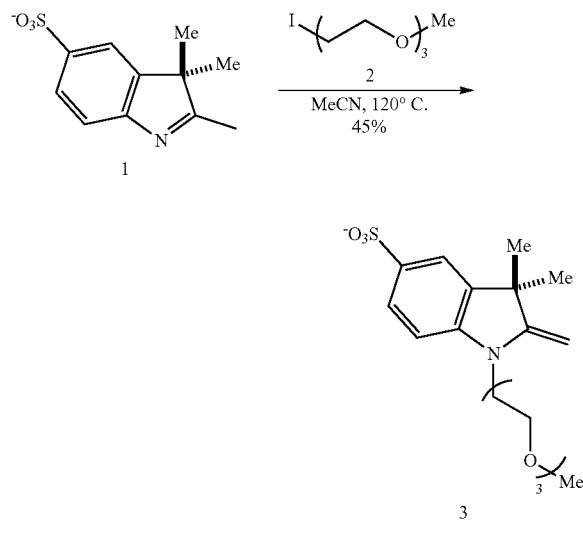

solvent removed by rotary evaporation. Water (10 mL) was added to the red crude and purified by reversed-phase chromatography ($C_{18}$ Aq, 0→30% MeCN/water). The product-containing fractions were combined and the solvent removed by rotary evaporation to afford 3 (2.1 g, 45% yield) as a red gummy solid. $^1$H NMR (400 MHz, DMSO-$d_6$ exists as 93:7 ratio of enamine:imine tautomers) δ 7.38-7.29 (m, 2H), 6.59 (d, J=8.0 Hz, 1H), 3.96 (d, J=1.9 Hz, 1H), 3.88 (d, J=1.9 Hz, 1H), 3.68 (t, J=6.0 Hz, 2H), 3.57 (t, J=6.0 Hz, 2H), 3.52-3.43 (m, 6H), 3.41-3.36 (m, 2H), 3.22 (s, 3H), 1.26 (s, 6H); $^{13}$C NMR (125 MHz, DMSO-$d_6$) δ 160.6, 145.7, 139.3, 135.7, 125.3, 119.4, 104.2, 74.7, 71.2, 70.1, 69.8, 69.6, 66.4, 58.0, 43.5, 41.9, 29.7; IR (thin film) 2921, 1715, 1650, 1604, 1486, 1382, 1182 cm$^{-1}$; HRMS (ESI) calculated for $C_{18}H_{28}NO_6S$ (M+H)$^+$ 386.1632, observed 386.1632.

To a microwave tube equipped with a magnetic stir bar was added indolenine 3

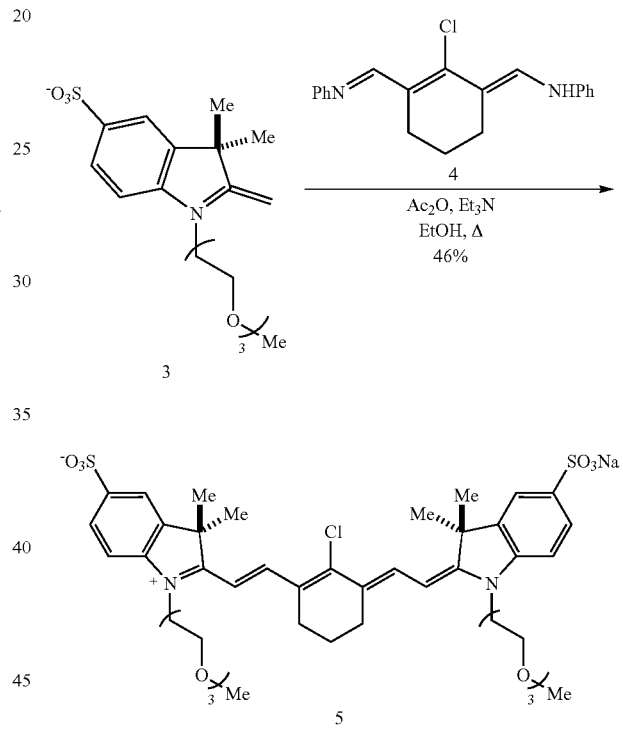

(2.07 g, 4.9 mmol) in ethanol (14 mL) and chloride 4 (0.45 g, 1.4 mmol). The vessel was sealed and flushed with argon. Triethylamine (1.37 mL, 9.8 mmol), and acetic anhydride (1.85 mL, 19.6 mmol) were then added in succession by syringe. The yellow solution was heated to 120° C. for 30 minutes, during which time the reaction transitioned to a deep green color. The reaction was cooled and the solvent removed by rotary evaporation. Saturated aqueous NaHCO$_3$ (17 mL) was added and the green residue was purified by reversed-phase chromatography ($C_{18}$, 0→30% MeCN/water). The product-containing fractions were lyophilized to afford 5 (1.04 g, 46% yield) as a green solid. $^1$H NMR (500 MHz, methanol-$d_4$) δ 8.46 (d, J=14.1 Hz, 2H), 7.92 (d, J=1.7 Hz, 2H), 7.88 (dd, J=8.3, 1.7 Hz, 2H), 7.40 (d, J=8.4 Hz, 2H), 6.49 (d, J=14.1 Hz, 2H), 4.41 (t, J=5.1 Hz, 4H), 3.91 (t, J=5.1 Hz, 4H), 3.60-3.57 (m, 4H), 3.53-3.50 (m, 4H), 3.48-3.44 (m, 4H), 3.41-3.37 (m, 4H), 3.28 (s, 6H), 2.75 (t, J=6.2 Hz, 4H), 2.00-1.91 (m, 2H), 1.77 (s, 12H); $^{13}$C NMR (125 MHz, methanol-$d_4$) δ 175.6, 151.4, 145.7, 145.3, 143.6, 142.4, 129.0, 128.0, 121.3, 112.4, 104.2, 72.9, 72.1, 71.7, 71.4, 69.2, 59.1, 50.7, 46.1, 28.3, 27.4, 22.1; IR (thin film) 2864, 1546, 1509, 1427, 1387, 1234, 1151 cm$^{-1}$; HRMS (ESI) calculated for $C_{44}H_{60}ClN_2O_{12}S_2$ (M+H)$^+$ 907.3271, observed 907.3268.

To a 1-dram vial equipped with a magnetic stir bar was added chloride 5 (100 mg, 0.108 mmol) and DMF (1.0 mL). 2-(Methylamino)-ethanol (35 μL, 0.43 mmol) was added and the reaction was heated to 75° C. for 15 minutes, during which time the reaction color transitioned from green to dark blue. The reaction was cooled and diluted with saturated aqueous NaHCO$_3$ (3 mL) and H$_2$O (7 mL), and the solution was directly purified by reversed-phase chromatography (C$_{18}$ Aq gold, 0→25% MeCN/water). The product-containing 1.79 (m, 2H), 1.67 (s, 12H); $^{13}$C NMR (125 MHz, DMSO-d$_6$) δ 176.1, 168.1, 143.2, 143.2, 140.7, 139.1, 125.7, 123.3, 119.3, 108.7, 95.9, 71.2, 70.3, 69.8, 69.7, 67.3, 59.6, 58.5, 58.0, 47.2, 44.1, 43.3, 28.7, 24.4, 21.5; IR (thin film) 3409, 2927, 2870, 1546, 1509, 1365, 1279, 1158 cm$^{-1}$; HRMS (ESI) calculated for $C_{47}H_{68}N_2O_{13}S_2$(M+H)$^+$ 946.4188, observed 946.4186.

To a 1-dram vial equipped with a magnetic stir bar was added chloride 5 (640 mg, 0.65 mmol) and DMF (18 mL). 3-(Methylamino)-1-propanol (250 μL, 2.54 mmol) was added and the reaction was heated to 100° C. for 25 minutes, during which time the reaction color transitioned from green to dark blue. The reaction was cooled and diluted with saturated aqueous NaHCO$_3$ (18 mL) and the solution was

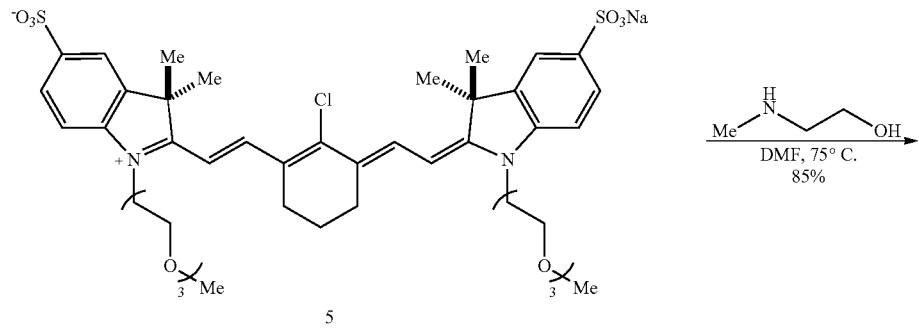

5

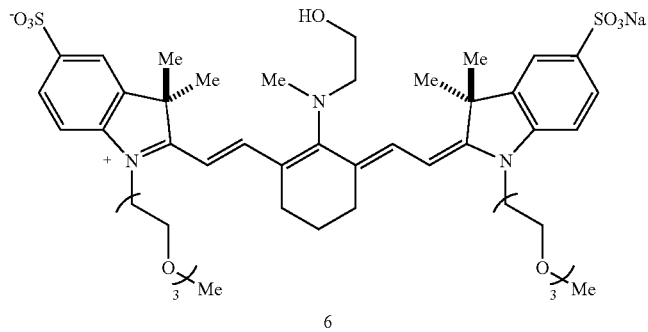

6 fractions were lyophilized to afford 6 (90 mg, 85% yield) as a blue solid. $^1$H NMR (400 MHz, methanol-d$_4$) δ 7.89-7.64 (m, 6H), 7.16 (d, J=8.5 Hz, 2H), 6.05 (d, J=13.2 Hz, 2H), 4.27-4.11 (m, 4H), 4.01-3.92 (m, 4H), 3.89-3.81 (m, 4H), 3.61-3.57 (m, 4H), 3.57-3.51 (m, 7H), 3.51-3.46 (m, 4H), 3.45-3.40 (m, 4H), 3.30 (s, 6H), 2.63-2.45 (m, 4H), 1.92- directly purified by reversed-phase chromatography (C$_{18}$ Aq gold, 0→40% MeCN/water). The product-containing fractions were lyophilized to afford 7 (616 mg, 74% yield) as a blue solid. $^1$H NMR (500 MHz, DMSO-d$_6$) δ 7.62 (d, J=1.7 Hz, 2H), 7.55 (dd, J=8.2, 1.7 Hz, 2H), 7.46 (d, J=13.3 Hz, 2H), 7.12 (d, J=

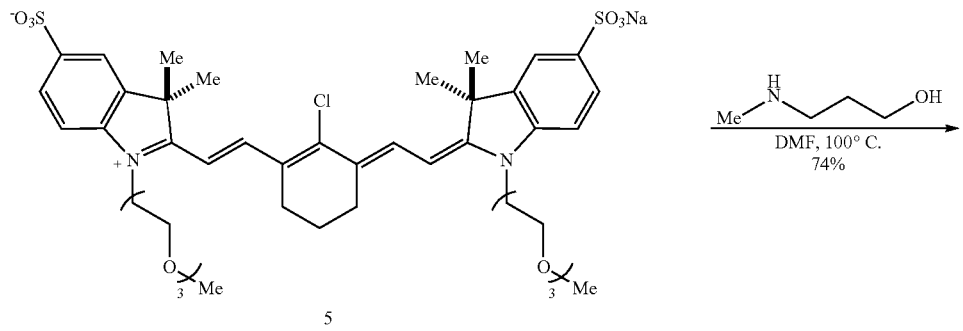

5

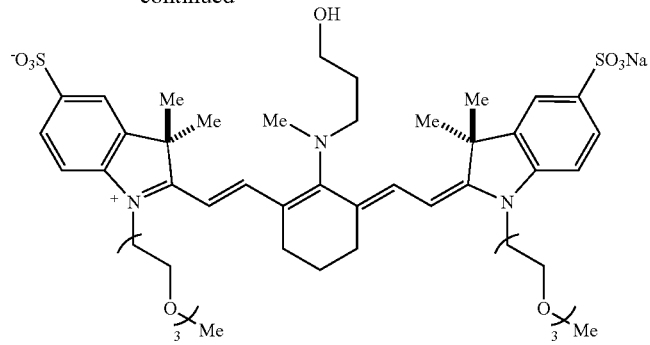

7

8.3 Hz, 2H), 5.98 (d, J=13.3 Hz, 2H), 4.61 (t, J=4.7 Hz, 1H), 4.24-4.14 (m, 4H), 3.90-3.80 (m, 2H), 3.78-3.69 (m, 4H), 3.53-3.50 (m, 4H), 3.49-3.39 (m, 14H), 3.33 (s, 3H), 3.18 (s, 6H), 2.49-2.46 (m, 4H), 1.91 (p, J=6.0 Hz, 2H), 1.74 (p, J=6.7 Hz, 2H), 1.58 (s, 12H); $^{13}$C NMR (125 MHz, DMSO-$d_6$) δ 174.9, 168.2, 143.3, 143.2, 140.4, 139.0, 125.8, 123.3, 119.4, 108.8, 96.0, 71.2, 70.3, 69.8, 69.7, 67.3, 58.1, 58.0, 55.6, 47.2, 44.8, 43.4, 31.5, 28.7, 24.3, 21.4; IR (thin film) 3410, 2926, 2870, 1543, 1366, 1279, 1160 cm$^{-1}$; HRMS (ESI) calculated for $C_{48}H_{70}N_3O_{13}S_2$ (M+H)$^+$ 960.4345, observed 960.4343.

To a microwave vial equipped with a magnetic stir bar was added cyanine 6 (70 mg, 0.11 mmol) and NaHCO$_3$ (61 mg, 0.72 mmol). DMF (1.5 mL) and methyl iodide (45 µL, 0.72 mmol) were added and the reaction was heated to 95° C. for 2 hours, during which time the reaction color transitioned from blue to green. The reaction was cooled and diluted with water (10 mL) and the solution was directly purified by reversed-phase chromatography (C$_{18}$ Aq gold, 0→30% MeCN/water). The product-containing fractions were lyophilized to afford 8 (60 mg, 86% yield) as a green solid. $^1$H NMR (500 MHz, DMSO-$d_6$) δ 7.87 (d, J=14.1 Hz, 2H), 7.74 (s, 2H), 7.67-7.59 (m, 2H), 7.35 (d, J=8.3 Hz, 2H), 6.29 (d, J=14.2 Hz, 2H), 4.47 (t, J=6.1 Hz, 2H), 4.39 (t, J=5.3 Hz, 4H), 3.95 (t, J=6.3 Hz, 2H), 3.79 (t, J=5.1 Hz, 4H), 3.54-3.48 (m, 4H), 3.45-3.35 (m, 12H), 3.31 (s, 9H), 3.18 (s, 6H), 2.60 (t, J=6.2 Hz, 4H), 1.85-1.73 (m, 2H), 1.67 (s, 12H); $^{13}$C NMR (125 MHz, DMSO-$d_6$) δ 172.2, 167.9, 145.3, 142.4, 140.1, 139.1, 126.0, 122.4, 119.5, 110.7, 101.0, 71.2, 70.3, 69.8, 69.6, 69.4, 67.5, 64.1, 58.0, 53.4, 48.6, 44.3, 27.8, 24.2, 20.5; IR (thin film) 2868, 1556, 1504, 1392, 1357, 1249, 1148 cm$^{-1}$; HRMS (ESI) calculated for $C_{49}H_{72}N_3O_{13}S_2$ (M+H)$^+$ 974.4501, observed 974.4506.

To a round bottom flask equipped with a magnetic stir bar was added cyanine 7 (620 mg, 0.11 mmol) and TFA (6 mL). The red solution was heated to 60° C. for 5 minutes under

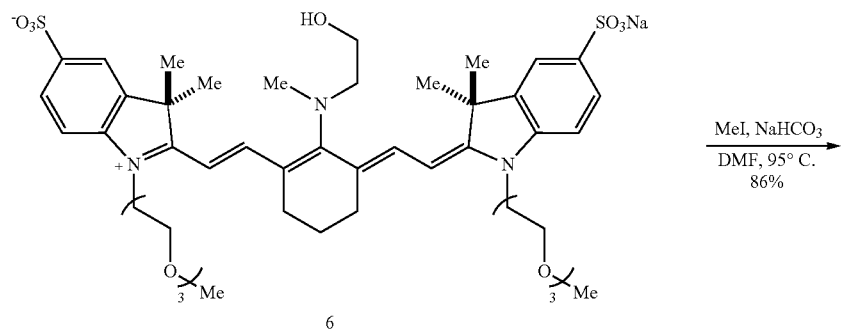

6

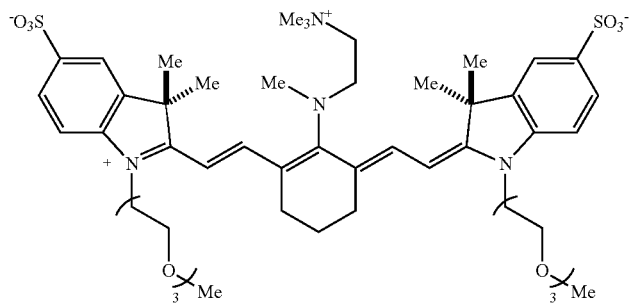

8

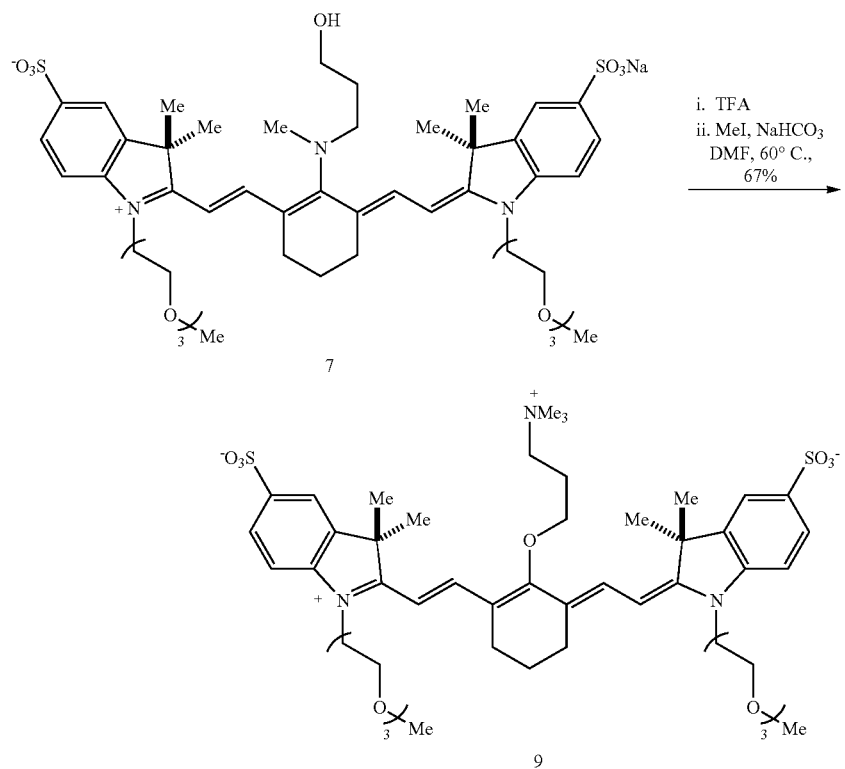

argon. The TFA was removed in vacuo and the residue was placed under vacuum (<0.1 Torr) for 5 minutes. DMF (20 mL), NaHCO$_3$ (2.6 g) and methyl iodide (2 mL) were added and the reaction was heated to 60° C. for 3 hours. The reaction was cooled and diluted with water (40 mL) and the solution was directly purified by reversed-phase chromatography (C$_{18}$ Aq gold, 0→40% MeCN/water). The product-containing fractions were lyophilized to afford 9 (420 mg, 67% yield) as a green solid. $^1$H NMR (500 MHz, DMSO-d$_6$) δ 7.94 (d, J=14.2 Hz, 2H), 7.80 (d, J=1.8 Hz, 2H), 7.63 (dd, J=8.1, 1.8 Hz, 2H), 7.33 (d, J=8.3 Hz, 2H), 6.28 (d, J=14.2 Hz, 2H), 4.37 (t, J=5.3 Hz, 4H), 4.03 (t, J=5.6 Hz, 2H), 3.79 (t, J=5.1 Hz, 4H), 3.76-3.70 (m, 2H), 3.53-3.49 (m, 5H), 3.44-3.36 (m, 8H), 3.33-3.30 (m, 4H), 3.26 (s, 9H), 3.18 (s, 6H), 2.62-2.54 (m, 4H), 2.44-2.36 (m, 2H), 1.84-1.76 (m, 2H), 1.69 (s, 12H); $^{13}$C NMR (125 MHz, DMSO-d$_6$) δ 172.2, 168.5, 145.2, 142.4, 140.1, 139.5, 126.0, 122.3, 119.7, 110.6, 100.8, 73.4, 71.2, 70.3, 69.8, 69.7, 67.5, 62.9, 58.0, 52.4, 48.6, 44.2, 39.5, 27.9, 24.2, 23.8, 20.7; IR (thin film) 2874, 1557, 1506, 1392, 1359, 1248, 1151 cm$^{-1}$; HRMS (ESI) calculated for C$_{50}$H$_{74}$N$_3$O$_{13}$S$_2$ (M+H)$^+$ 988.4658, observed 988.4660.

VII.i.b. BL-760.

First, a BL-760 intermediate was created. Commercially available IR Dye 783 (120 mg, 0.16 mmol) was dissolved in dry DMF (2 mL) in a microwave tube equipped with a magnetic stir bar and sealed. The solution was flushed with argon for 2 min, followed by addition of 2-(methylamino)ethanol (65 µl, 0.8 mmol). The solution was heated to 80° C. in a sand bath during which time the color changed from green to blue and LC-MS indicated formation of the desired product. The reaction mixture was cooled, precipitated into Et$_2$O and

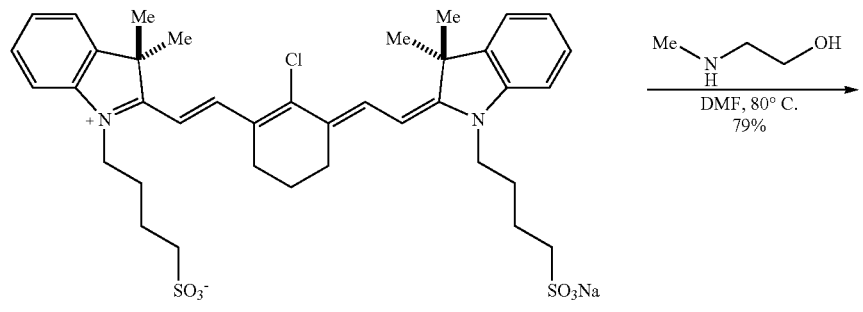

IR-Dye 783

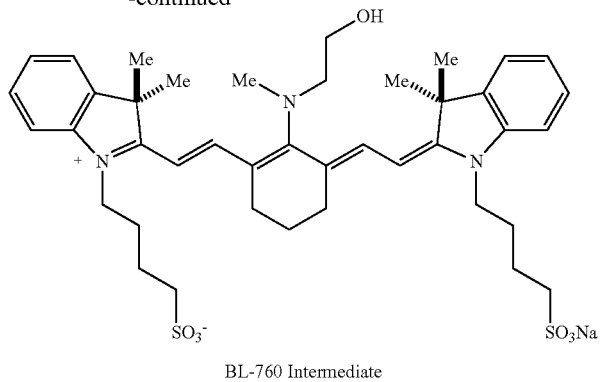

BL-760 Intermediate centrifuged for 3 min at 4500 rpm. Water (2 mL) and aqueous saturated NaHCO$_3$ solution (2 mL) were added to the pellet and the residue was purified by reversed-phase chromatography (C$_{18}$, 0→40% MeCN/H$_2$O). The product containing fractions were combined and lyophilized to afford BL-760 intermediate (99 mg, 79% yield) as a blue solid. $^1$H NMR (400 MHz, Methanol-d$_4$) δ 7.77 (d, J=13.3 Hz, 1H), 7.37 (d, J=7.4 Hz, 1H), 7.32 (t, J=7.7 Hz, 1H), 7.16 (d, J=8.0 Hz, 1H), 7.11 (t, J=7.5 Hz, 1H), 5.96 (d, J=13.4 Hz, 1H), 4.1-4.0 (m, 4H), 3.95-3.85 (m, 4H), 3.53-3.39 (m, 4H), 2.87 (t, J=6.8 Hz, 4H), 2.55 (t, J=6.6 Hz, 4H), 2.05-1.86 (m, 8H), 1.85 (t, J=6.5 Hz, 2H), 1.65 (s, 12H) ppm.

Next, BL-760 was created by combining HATU (61 mg, 0.16 mmol), acetic acid (10 μl, 0.17 mmol) and dry DMF (2.8 mL) in a 1-dram vial and flushed with argon. DIPEA (31 μl, 0.17 mmol) was added and the solution was stirred at r.t. for 10 min. In a separate 1-dram vial, BL-760 Intermediate was dissolved in dry DMF (2.1 mL) and flushed with argon. To this solution was added 1.4 mL of the activated ester solution and the solution was heated to 35° C. in a sand bath overnight, during which time the color changed from blue to green. The solution was cooled, precipitated into Et$_2$O and centrifuged for 3 min at 4500 RPM. The pellet was dissolved in water (5 mL) and the solution was directly purified by reversed-phase chromatography (C$_{18}$, 0→40% MeCN/H$_2$O). The product containing fractions were combined and lyophilized to afford BL-760 (53 mg, 80% yield) as a bluish green solid. $^1$H NMR (400

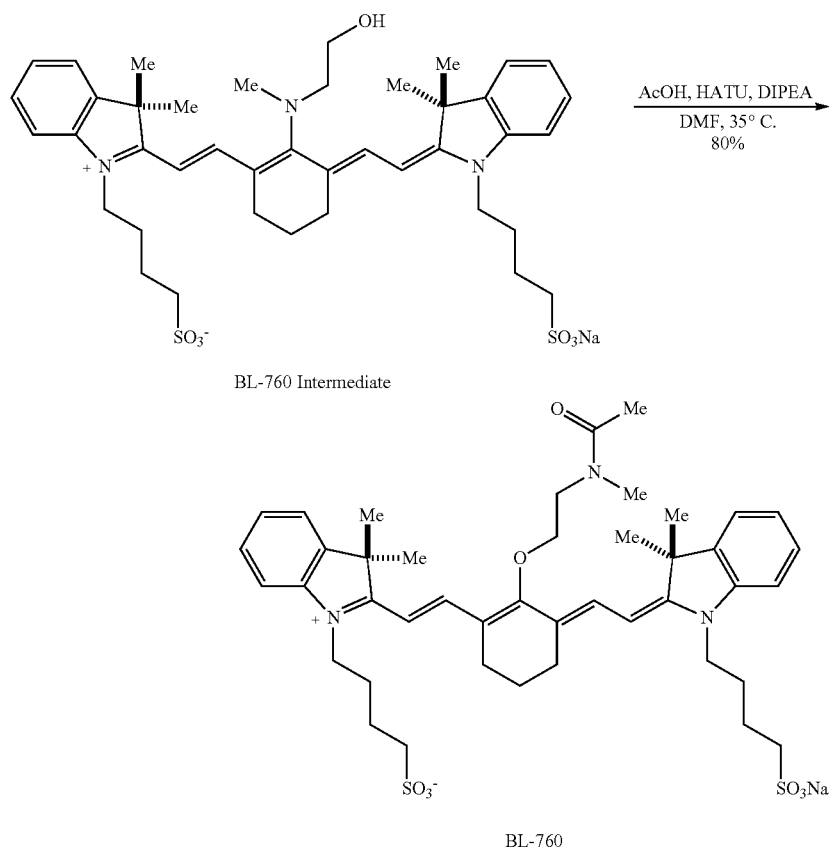

Figure 8:
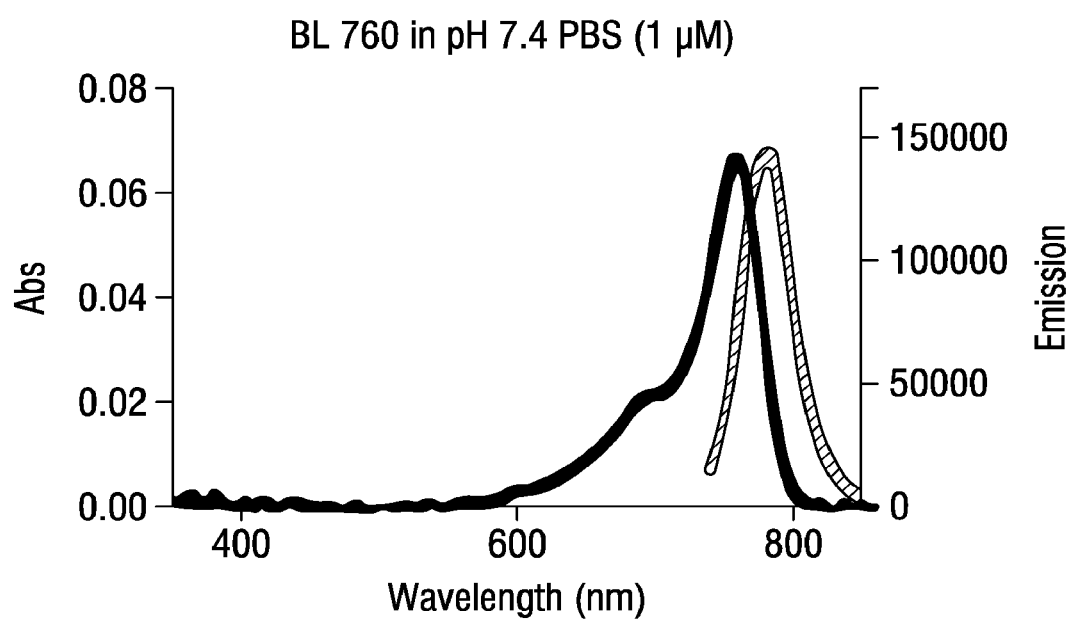
FIG. 8 is a graph showing the spectroscopic properties of the BL-760 compound, according to an exemplary embodiment of the present disclosure.

MHz, Methanol-d$_4$, compound exists as a mixture of rotamers, major rotamer is designated by *, minor rotamer denoted by §) δ 8.14 (two overlapping d, J=14.2 Hz, 2H*, 2H§), 7.49 (dd, J=7.5, 1.1 Hz, 2H*, 2H§), 7.44-7.37 (m, 2H*, 2H§), 7.35-7.31 (m, 2H*, 2H§), 7.24 (tdd, J=7.4, 1.9, 1.0 Hz, 2H*, 2H§), 6.22 (d, J=5.9 Hz, 2H*), 6.19 (d, J=5.8 Hz, 2H§), 4.25-4.08 (m, 6H*, 6H§), 4.07-3.87 (m, 2H*, 2H§), 3.29 (s, 3H*), 3.20 (s, 3H§), 2.88 (td, J=7.2, 1.7 Hz, 4H*, 4H§), 2.66 (q, J=5.7 Hz, 4H*, 4H§), 2.29 (s, 3H*), 2.22 (s, 3H§), 2.03-1.89 (m, 10H*, 10H§), 1.74 (s, 12H*), 1.70 (s, 12H§) ppm. FIG. 8 shows the spectroscopic properties of BL-760 in pH 7.4 PBS.

VII.ii. In Vitro Compound Characterization

Flash column chromatography was performed using reversed phase (100 Å, 20-40 micron particle size, RediSep® Rf Gold® Reversed-phase C18 or C18Aq column) on a CombiFlash® Rf 200i system (Teledyne Isco, Inc.). High-resolution LC/MS analyses were conducted on a Thermo-Fisher LTQ-Orbitrap-XL hybrid mass spectrometer system with an Ion MAX API electrospray ion source in negative ion mode. Analytical LC/MS was performed using a Shimadzu LCMS-2020 Single Quadrupole system utilizing a Kinetex 2.6 μm C18 100 Å (2.1×50 mm) column obtained from Phenomenex, Inc. Runs employed a gradient of 0→90% MeCN/0.1% aqueous formic acid over 4.5 min at a flow rate of 0.2 mL/min. $^1$H NMR and $^{13}$C NMR spectra were recorded on Bruker spectrometers (at 400 or 500 MHz or at 100 or 125 MHz) and are reported relative to deuterated solvent signals. Data for $^1$H NMR spectra are reported as follows: chemical shift (δ ppm), multiplicity, coupling constant (Hz), and integration. Data for $^{13}$C NMR spectra are reported in terms of chemical shift. IR spectra were recorded on a Jasco FT/IR-4100 spectrometer and are reported in terms of frequency of absorption (cm$^{-1}$). Absorption curves for quantum yield measurements were performed on a Shimadzu UV-2550 spectrophotometer operated by UVProbe 2.32 software. Fluorescence traces were recorded on a PTI QuantaMaster steady-state spectrofluorimeter operated by FelixGX 4.2.2 software, with 5 nm excitation and emission slit widths, 0.1 s integration rate, and enabled emission correction. Data analysis and curve fitting were performed using Microsoft® Excel 2011 software and GraphPad Prism 7 software. Light intensity measurements were performed with a Thorlabs PM200 optical power and energy meter fitted with an S120VC standard Si photodiode power sensor (200-1100 nm, 50 nW-50 mW). Flow cytometry was performed at the CCR Flow Cytometry Core (NCI-Frederick) and microscopy was performed at the Optical Microscopy and Analysis Laboratory (NCI-Frederick). See *JOC Standard Abbreviations and Acronyms* for abbreviations (http://pubs.acs.org/uscrimages/ContentEditor/1218717864819/joccah_abbreviations.pdf).

To perform stability studies, stock solutions (5 mM) of 7, 9, and IR-800CW compound were initially prepared in DMSO. A five hundred-fold dilution in 50 mM PBS buffer (pH=7.4) was performed to yield 10 μM samples. The samples were analyzed by HPLC (t=0 min) and 5 μL of a 0.2 M glutathione solution in de-ionized water was added to afford a 1 mM final glutathione concentration. The samples were continuously analyzed every 20 minutes by HPLC, and the integrated peak areas of absorbance at 780 nm from the starting dyes were plotted versus time. The sample was analyzed on an Agilent 1260 Infinity HPLC utilizing a Symmetry® 300 C18 3.5 μm 100 Å (2.1×100 mm) column (Waters, P/N 186000188) with a gradient of 2-98% (7 min) MeCN/10 mM ammonium bicarbonate at a flow rate of 0.8 mL/min. To confirm the formation of the glutathione adduct of IR-800CW compound, IR-800CW compound (50 μM) was incubated with or without glutathione (1 mM) for 24 h in pH 7.4 PBS. The formation of the MS adduct ([M/2]$^-$) was only observed with glutathione.

To perform cell culture characterization of each compound, isolation of whole-cell lysate and gel-based analysis of cyanine reactivity, HEK293 cells were first cultured at 37° C. under 5% CO$_2$ atmosphere in a growth medium of DMEM supplemented with 10% FBS and 2 mM glutamine. Cells were harvested at 80-90% confluency by washing cells 3× with ice cold PBS, scraping cells into a Falcon™ tube, centrifuging (1400 rcf×3 min, 4° C.) to form a cell pellet and removing the PBS supernatant. For lysis, cells were first resuspended in 1 mL ice cold PBS (10-20×10$^6$ cells/mL) containing protease inhibitor cocktail (1×, EDTA-free, Cell Signaling Technology #5871S) and PMSF (1 mM, Sigma #78830), and then lysed by sonication using a 100 W QSonica XL2000 sonicator (3×1 s pulse, amplitude 1, 60 s resting on ice between pulses). Lysate was pelleted by centrifugation (14,000 rcf×30 min, 4° C.), quantified on a Qubit® 2.0 Fluorometer using a Qubit® Protein Assay Kit and diluted to 2 mg/mL. For gel-based analysis of cyanine reactivity, 20 μg of HEK293 lysate was treated with 10 μM cyanine dyes for 24 h at room temperature, loaded onto a 4-12% SDS-PAGE gel and electrophoretically separated according the manufacturer's instructions. Gels were visualized using an Odyssey® CLx imager (LI-COR) with NIR laser excitation (700 nm and 800 nm emission channels) and Coomassie stain.

The thiol reactivity of compounds 8 and 9 were evaluated. FNIR-774 (a C4'-O-alkyl cyanine) is nearly immune to thiol-substitution reactions as shown below, while C4'-phenol variants are known to readily undergo thiol exchange (Nani et al., *Organic Letters* 2015, 17(2):302-305).

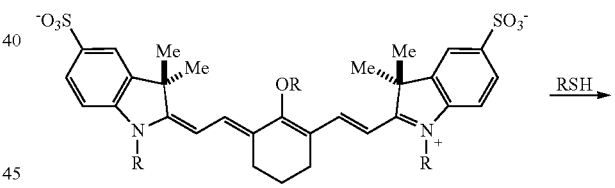

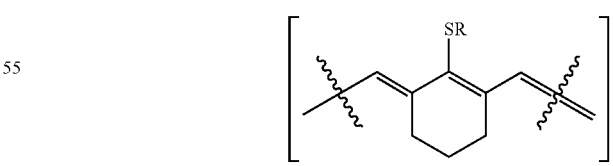

Figure 9:
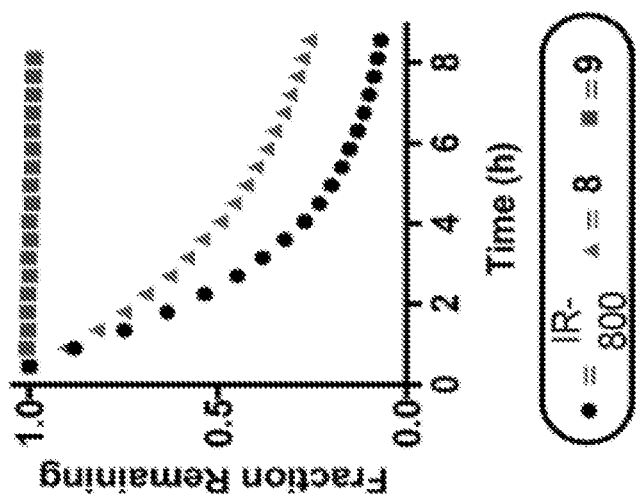
FIG. 9 is a graph showing glutathione stability of heptamethine cyanines as a fraction of starting cyanine as a function of time, according to an exemplary embodiment of Formula I of the present disclosure.

The reactivities of compounds 8, 9, and the IRDye® 800CW compound were compared in 1 mM glutathione (GSH) in pH 7.4 PBS using an HPLC assay (FIG. 9). FNIR-774 was not subject to thiol addition under identical conditions.

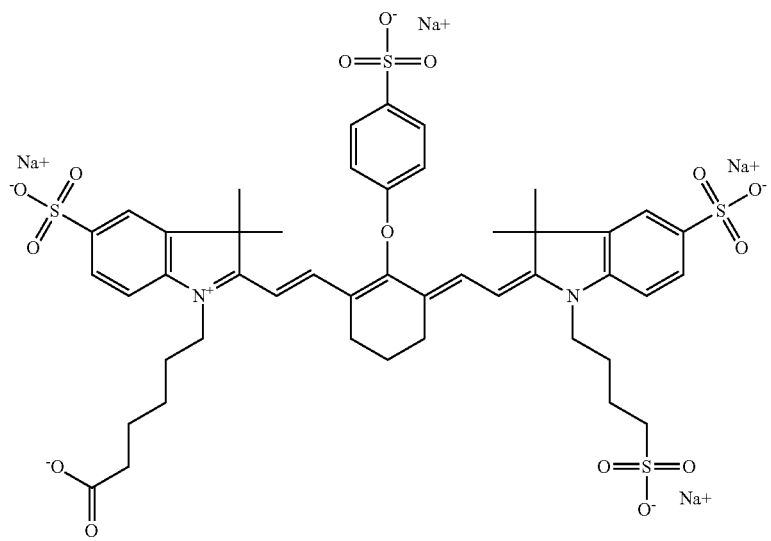

(IRDye ® 800 CW compound)

The IRDye® 800CW compound was consumed with an approximate half-life ($t_{1/2}$) of 2 h, with clean formation of the resulting GSH adduct observed by mass spectral analysis. Somewhat surprisingly, and unlike some other prior C4'-alkyl ether cyanines, the ethyl linker variant 8 was subject to the same reaction, albeit with moderately slower kinetics under identical conditions. However, compound 9, which has a propyl linker to the trimethyl-ammonium functional group, was unreactive in these conditions, with >95% of starting material surviving after 12 h incubation at rt. This result suggests that C4'-O-alkyl cyanines can undergo thiol exchanges in certain cases when strong-electron withdrawing functional groups are appended in the β-, but apparently not the γ-, position.

Figure 10:
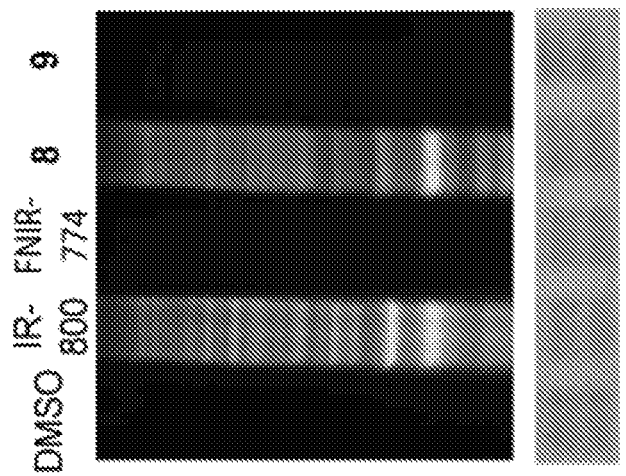
FIG. 10 is a photograph of a gel showing proteome-wide reactivity of cyanines to HEK-293 cells, according to an exemplary embodiment of the present disclosure.

The thiol-substitution reaction in cellular proteome was evaluated. Whole-cell lysate, obtained from HEK-293 cells, was incubated with compounds 8, 9, FNIR-774, and the IRDye® 800CW compound for 24 hours at room temperature. The mixture was then run on an SDS-page gel and the 800 nm fluorescence emission was imaged. This approach allows for visualization of proteins modified covalently by a cyanine fluorescent scaffold. As shown in (FIG. 10), compound 8 and the IRDye® 800CW compound show dramatic labeling. Labeling was not observed with compound 9 and FNIR-774. Consistent with the notion that these fluorescent bands result from heptamethine cyanine labeling, no meaningful signal was observed with 700 nm excitation. These studies provide the first evidence that C4'-phenol-substituted cyanines can react with cellular proteins, presumably via the S-alkylation pathway described above, rendering them less desirable for in vivo applications.

VII.iii. In Vivo Compound Characterization

Embodiments of the disclosed heptamethine cyanines according to Formula I and Formula II may be used for in vivo visualization of at least a portion of a subject's renal system or biliary system. A suitable pharmaceutical composition comprising the heptamethine cyanine can be administered to the subject. Following administration, at least a portion of the subject's renal and/or biliary system can be irradiated with an effective quantity of near-IR radiation and an image is obtained, whereby organs and/or structures of the renal system and/or biliary system are visualized. Irradiation can be performed externally or internally. When external irradiation is desired, the surface area can be controlled with an appropriate light applicator, e.g., a microlens, Fresnel lens, or diffuser. When internal radiation is desired, an endoscope or a fiber optic catheter may be used. When visualization of the renal system is desired, the heptamethine cyanine may have a structure according to Formula I or Formula IA. When visualization of the biliary system is desired, the heptamethine cyanine may have a structure according to Formula II or Formula IIA.

Embodiments of the disclosed heptamethine cyanines according to Formula I and Formula II may be used for in vivo visualization of a subject's renal system or biliary system during surgery, e.g., abdominal and/or pelvic surgery. A suitable pharmaceutical composition comprising the heptamethine cyanine can be administered to the subject. A portion of the subject's renal and/or biliary system can be irradiated with an effective quantity of near-IR radiation and an image can be obtained, whereby organs and/or structures of the renal system and/or biliary system are visualized. Irradiation can be performed externally or internally as described above. External irradiation may include external irradiation through the subject's skin or direct external irradiation of the organs of interest, e.g., during an open surgical procedure. Internal irradiation may be used, e.g., during a minimally invasive or laparoscopic procedure. In an embodiment, the heptamethine cyanine can be administered to the subject during surgery or just prior (e.g., 5-30 minutes prior) to surgery. When visualization of the renal system is desired, the heptamethine cyanine may have a structure according to Formula I or Formula IA. When visualization of the biliary system is desired, the heptamethine cyanine may have a structure according to Formula II or Formula IIA.

VII.iii.a. UL-766 Evaluation in Animals—Sprague Dawley Rats

Children's National Hospital animal care and use committee approved the protocol (IACUC #30597). All procedures were performed in the Research Animal Facility at Children's National Hospital. Female 250-300 g Sprague- Dawley rats from Charles River Laboratories (Wilmington, Mass., USA) were used for this experiment. A 3 minute inhalation of 4% isoflurane was used for sedation and restraint. Anesthesia was maintained using an intramuscular injection of 2 mg/kg xylazine and 75 mg/kg ketamine. After ensuring sterile conditions, a laparotomy was performed. For fluorescence imaging, a 24 G catheter was placed in the tail vein and 90 µg/kg injection was performed and immediately imaged after injection.

To enable both color and fluorescence image recording, an existing surgical microscope OPMI S5 (Karl Zeiss, Germany) was used with additional two camera ports. The microscope includes a 250-mm focal length main objective lens and two camera ports located both on the left and right arms split by a virtual beamsplitter integrated into the main body of the scope. CAM1 (GS3-U3-41C6C-C, FLIR, U.S.) was used for HD color vision, which operates at 30 frames per second with 2048×2048 pixels. CAM2 (GS3-U3-41C6NIR-C, FLIR, U.S.) was used for NIR fluorescence imaging, which includes a band-pass filter (790/30 nm) and also operates at 30 frames per second with the same 2048×2048 pixels. For illumination, a built-in microscope illuminator with a short-pass filter (cut-off wavelength: 800 nm) was used. For simultaneous visualization and recording, all the scripts for the camera control were custom built and programmed in a Linux operating machine.

Ureteral imaging and quantitative assessment: For open surgery, a standard midline laparotomy was performed. For fluorescence imaging, a 24 G catheter was placed in the tail vein and 90 µg/kg injection was performed and immediately imaged after injection. Imaging system was positioned and videos were recorded in real time up to 2 hrs. All images were acquired with a 33-ms exposure time. The ratio between fluorescence signal and background signal over a region of interest was quantified using ImageJ software. The contrast-background ratio (CBR) was calculated and plotted over time. Results were presented as mean+/−standard error of the mean (SEM).

Figure 11:
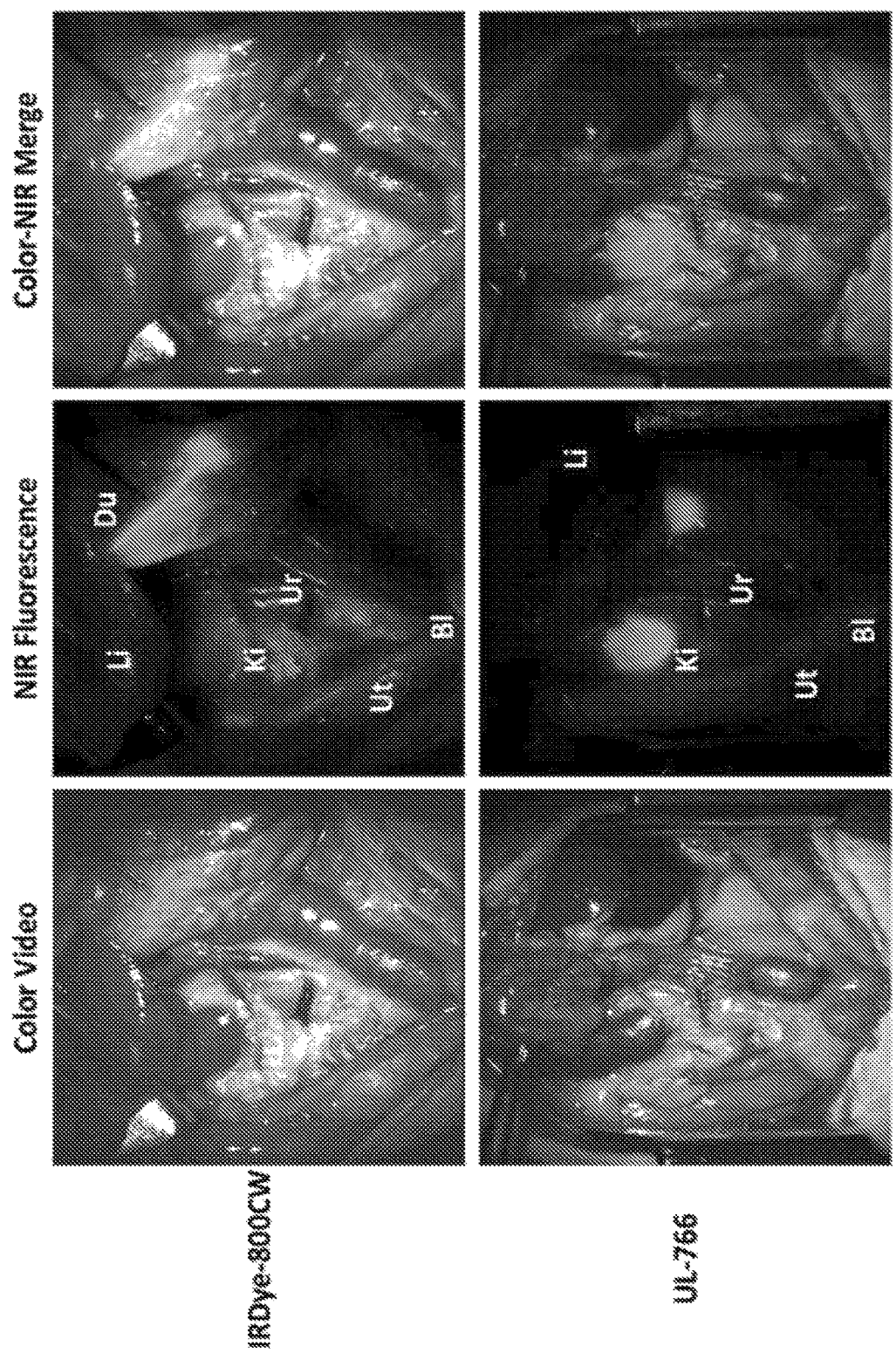
FIG. 11 is a series of images showing near-infrared fluorescence-guided intraoperative identification of the ureter using the IRDye® 800CW compound and UL-766, according to an exemplary embodiment of the present disclosure.

The in vivo biodistribution and clearance of compound 9, or Ureter Label-766 (UL-766), was evaluated and compared to IR-800CW compound. The two compounds were injected intravenously (0.09 mg/kg) into rats, the behavior of the injected compounds was monitored in real-time over 60 min. Details of the procedures and imaging studies are described above. As shown in FIG. 11, the IRDye® 800CW compound exhibited a complex biodistribution, being mostly found in the bile duct, intestine, and kidney. On the contrary, UL-766 demonstrated nearly exclusive renal clearance, with no visible nonspecific background signal in any organs other than the kidney or ureter.

Figure 12:
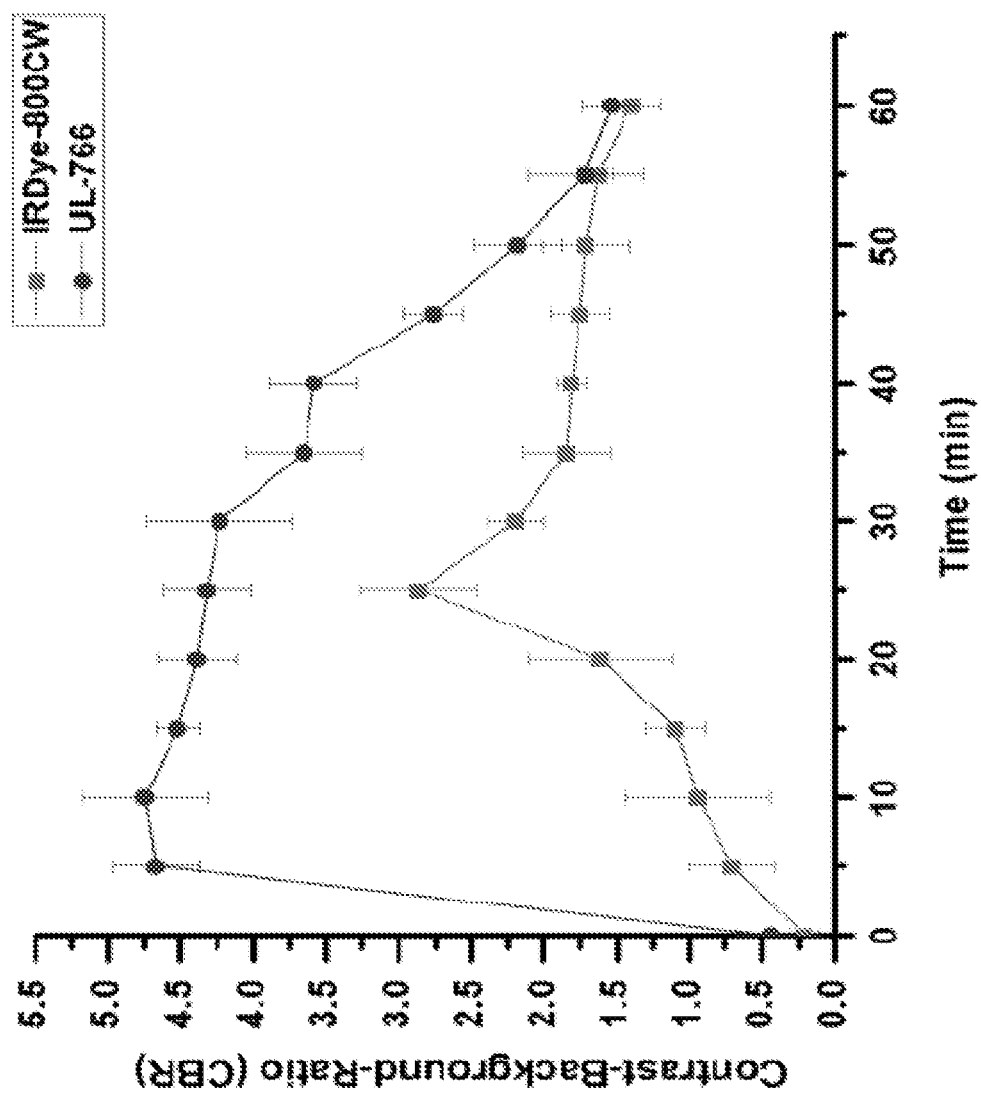
FIG. 12 is a graph showing the contrast-background ratio over time of kidney fluorescence in rats following injection with the IRDye® 800CW compound and UL-766, according to an exemplary embodiment of the present disclosure.

FIG. 12 shows the contrast-background-ratio (CBR) of kidney fluorescence over time with the IRDye® 800CW compound and UL-766. Based on these curves, the CBR is typically over 2× higher in UL-766 than for the IRDye® 800CW compound. Moreover, the time window for ureter visualization was much longer and started nearly immediately after injection of UL-766.

Figures 2, 13A:
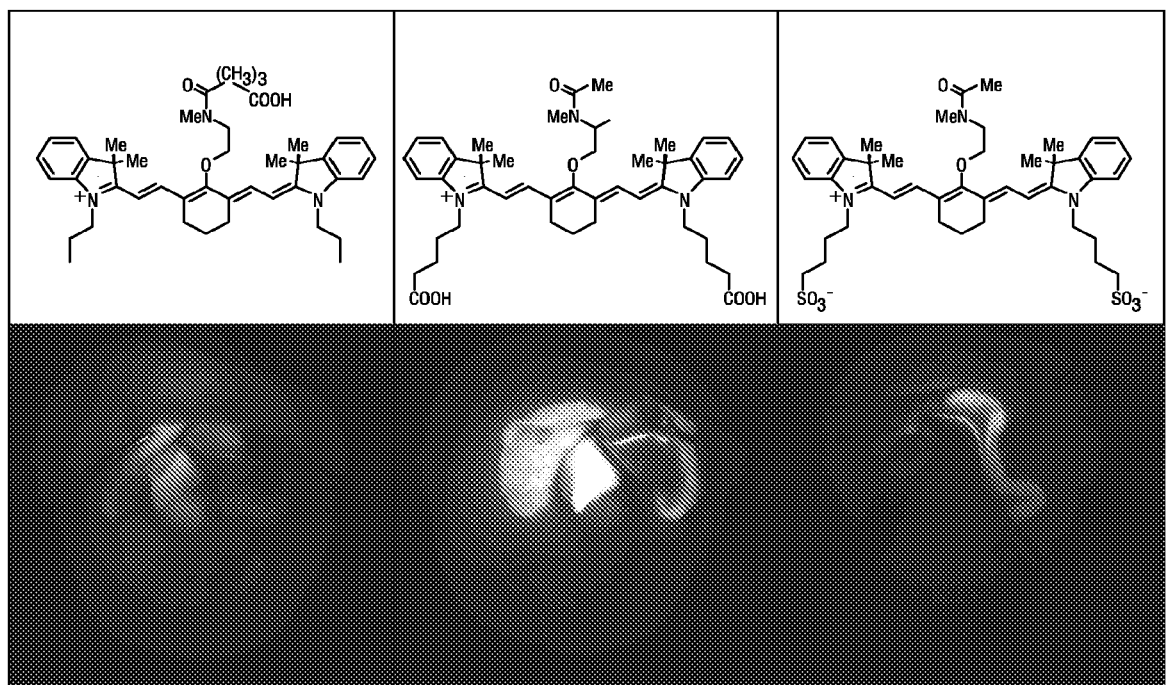

Commercially available dyes (indocyanine green (ICG), IRDye® 800CW compound) as well as several heptamethine cyanines including compounds according to Formula I (UL-766) and Formula II (Nac-Aryll-H_N-BS, also referred to as BL-760) were evaluated for excretion into bile and biliary:urinary specificity when injected into rats as described above. Images were obtained 10 minutes post-injection. The results are shown in FIGS. 13A and 13B. Strikingly, only UL-766 demonstrated high (95%) urinary specificity with little or no excretion into bile and a quantum yield of 30%. Indeed, UL-766 was the only compound with greater than 40% renal system specificity. Two other compounds, FNIR-Ar-H_N-BS and Nac_Aryll-H_N-BS (BL-760), showed high (95-100%) biliary specificity with rapid excretion—within 5 minutes—into bile and quantum yields of at least 20%. Although some other compounds also exhibited biliary specificity, excretion was very slow and/or quantum yield was low. For example, FDA-approved ICG is biliary specific, but has a biliary excretion time of 4 hours and a quantum yield of only 9%. The IRDye® 800CW compound excretes rapidly into bile but has a biliary:urinary specificity of 60:40, resulting in unacceptably high nonspecific fluorescence.

VII.iii.b. UL-766 Evaluation in Animals—Swine

Broadly, the study evaluated the utility of UL-766 in laparoscopic surgery. Moreover, the study evaluated the abilities of UL-766 to aid in ureteral visualization despite active inflammation. The capabilities of the dye to aid in ureteral visualization in a swine model with abdominal inflammation while utilizing a clinically-available laparoscopic fluorescent system.

UL-766 dye was synthesized as described above and was stored at −20° C. until experiments were begun.

The laparoscopic system was an FDA-cleared laparoscopic fluorescent imaging system (Model-L, InTheSmart Incorporated, USA). The system is capable of concurrent white-light and near-infrared imaging with dual light source (ITSEL1711, InTheSmart Incorporated, USA).

Two female Yorkshire pigs (weight 20-30 kg) were used. In the initial procedure, inflammation was created in the right retroperitoneum. Each pig was intubated and placed under isofluorane anesthesia before being positioned in the left lateral decubitus position. The abdomen was prepared and, after inserting four trocars, the right ureter was carefully dissected from its surrounding tissue by blunt dissection and electrocautery. This started at the level of the right inferior renal margin down to the ureteral insertion into the bladder. Care was taken not to devitalize the ureter from perfusing vessels. A gauze role was then used to further abrade the ureter and surrounding retroperitoneal tissue with strokes over the tissue until petechial hemorrhages were seen. After sufficient abrasion, the trocars and cause were removed.

Inflammation was allowed to develop and the pigs were returned to the operating room seven days after initial surgery. The right retroperitoneum was illuminated with both NIR and white light to provide the fusion visualization on the laparoscopy system. The UL-766 dye was diluted in 10 mL sterile water and given at 120 µg/kg by injection into an ear vein catheter with running normal saline infusion at the rate of 20 mL/kg/hr. Once visualization of the ureters was achieved by the UL-766 dye, the ureter was dissected from its surrounding tissue, starting from the level of the interior renal pole to the insertion in to the bladder. Fluorescent signal was monitored for up to 4 hours after initial injection. At the end of the experiment, ureteral injuries, by partial and complete transection were made by scissors with confirmation as effluence of urine into the peritoneum.

CBR was defined as the ratio of fluorescence intensity at the structure of interest to that of nearby tissue. The CBR of the UL-766 dye was calculated as $$CBR = \frac{(\text{Fluorescent intensity at ureter} - \text{Background Intensity})}{\text{Background Intensity}},$$

where background intensity is the fluorescent signal measured at the tissue of the retroperitoneum tissue. Essentially, the CBR helps describe how well the signal is localized t a specific tissue. A dye with high CBR creates a strong contrast as minimal to no fluorescent signal at surrounding tissues against the highly fluorescent target.

In the first pig, visualization of the ureter was achieved 7 minutes after dye injection. Visualization of ureter was fully achieved at 5 minutes after dye injection of the second pig. As expected, the fluorescent signal from the ureters was only visible when urine is present within the ureteral lumen. The fluorescent bolus of urine can be seen to travel from the renal pelvis along the length of the ureter and into the bladder. Fluorescent signal was seen in the kidneys before the presence of ureteral signals. The peak CBRs at these organs are listed in Table 2. Of note are the average CBR values at the ureter—38.56 and 14.5—at 10 minutes and 4 hours, respectively, after dye injection.

TABLE 2

Average Contrast-Background Ratio of Urinary Tract After UL-766 Injection

| | Time After injection | |
|---|---|---|
| | 10 minutes | 4 hours |
| Kidney | 17.96 | 11.20 |
| Ureter | 38.56 | 14.50 |
| Bladder | 1.49 | 2.98 |

The creation of retroperitoneal inflammation was successful. In Pig 2, the inflammation was enough to have caused an adhesive band development that led to a mild degree of obstruction at the ureter just distal the renal pelvis. The fluorescent signal was sued to guide dissection of the surrounding inflammatory tissue to free the ureter. In both pigs, the inflamed ureters were successfully isolated form its surrounding tissue.

VII.iii.c. BL-760 Evaluation in Animals—Sprague-Dawley Rats and Swine

BL-760, along with an additional four heptamethine cyanines was tested. Each was prepared at stored at −20° C. for use in the animal experiments. Relative brightness was determined using a 1 mg/mL solution on a surgical microscope. Each of the drugs was administered intravenously to the rats (dose rate: 90 µg/kg) in order to visualize the biodistribution of the compound.

Female 25-300 gram Sprague-Dawley rats were used. A laparotomy was performed. For fluorescent imaging, a 24 G catheter was placed in the tail vein and injection of the fluorophore (90 µg/kg) was performed, with immediate imaging after injection. An imaging system was set up and videos were recorded in real time until 3 hours after injection of the fluorophore. Target to background (TBR) noise, or (Target-Noise)/(Background-Noise), was calculated, wherein the background is normal adjacent liver parenchymal tissue and the target is the CBD. Noise was used in a region outside the target and background.

To better model a minimally-invasive experience, laparoscopic imaging was performed on female Yorkshire pigs (25-30 kg). Midline laparotomy was performed. At the beginning of the procedure, Calot's triangle was exposed and imaged. After 2 hours of imaging, a left lobectomy was performed using electrocautery to visualize the intrahepatic duct alongside the liver parenchyma. A laparoscopic system was set up and videos were recorded over the 3 hours after injection of the fluorophore. CBR was calculated.

Figure 14:
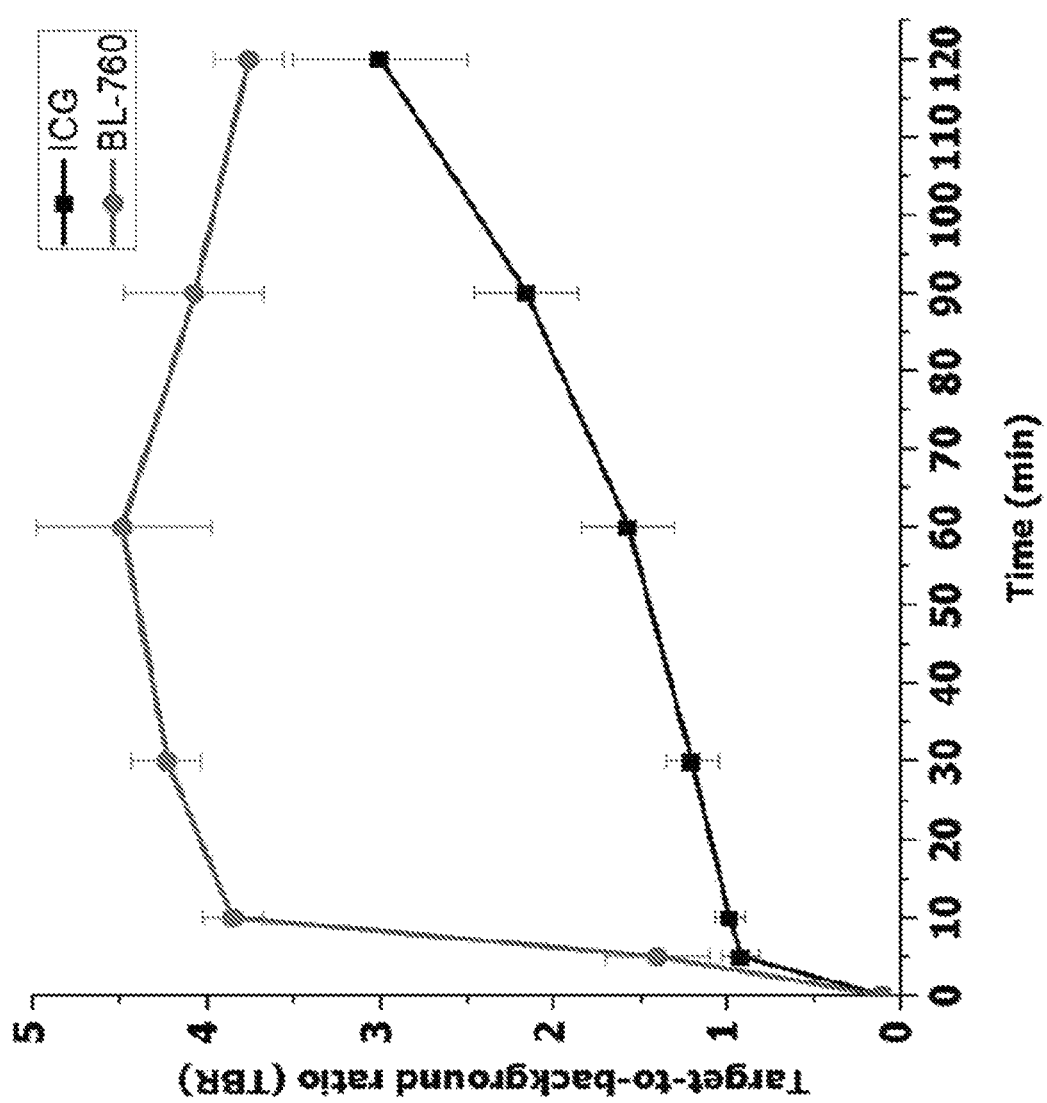
FIG. 14 is a graph showing the contrast-background ratio over time of kidney fluorescence in pigs following injection of BL-766 and ICG, according to an exemplary embodiment of the present disclosure.

After IV dye injection (90 µg/kg) into the pigs, the fluorescence signals from both ICG and BL-760 were acquired and recorded by the laparoscopic image system. First, BL-760 fluorescence signals in the cystic duct were compared to those of ICG at a similar post-injection time point. After intravenous injection, within 5-10 minutes, the cystic ducts were successfully visualized in both pigs. As can be seen in FIG. 14, BL-760 shows high TBR contrast between the bile duct and the liver parenchyma, compared to ICG, at a time of 9 minutes post injection. This contrast was sustained at 2 hours after injection.

Figure 15:
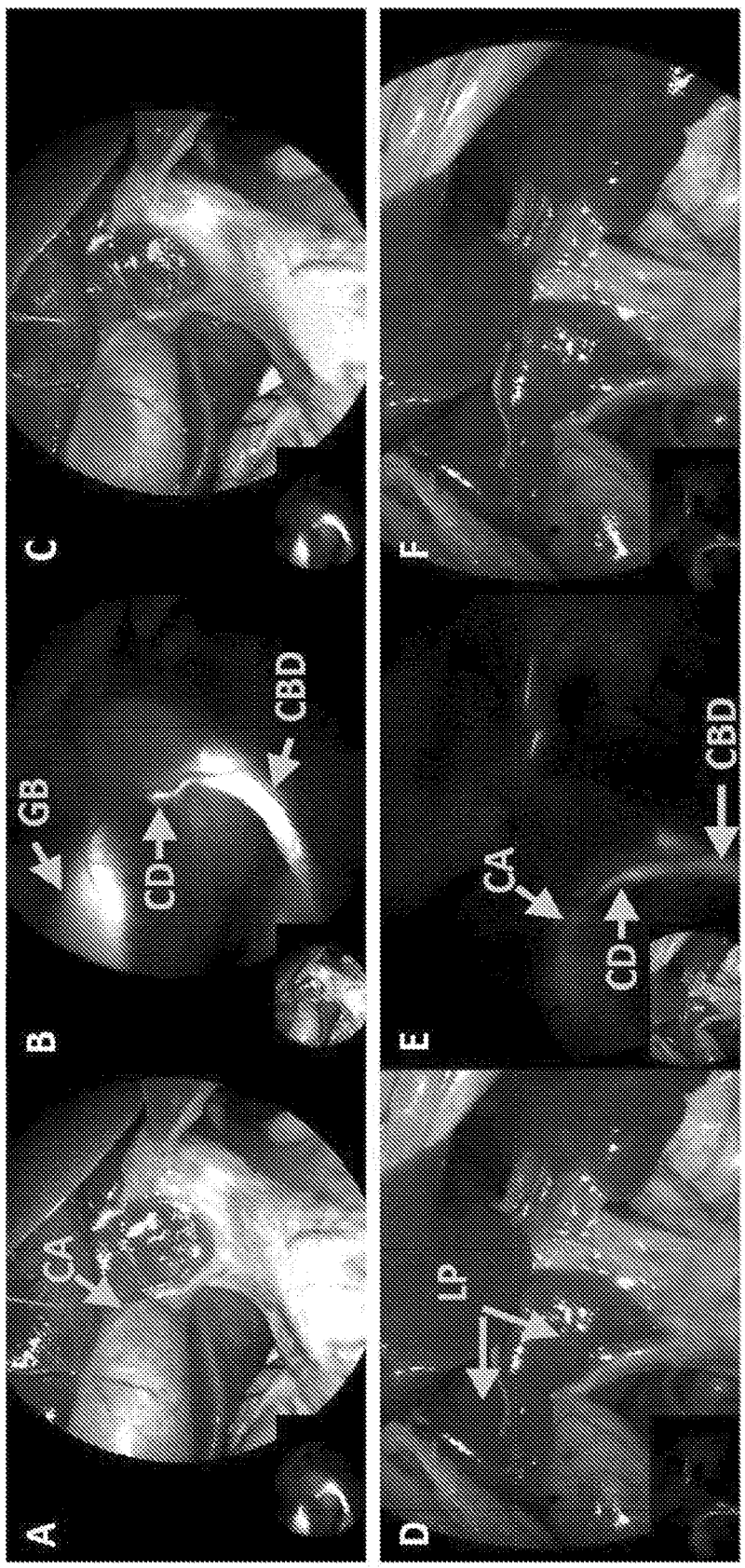
FIG. 15 is a panel of illustrations demonstrating the visualization of the gallbladder and cystic ducts in pigs, according to an exemplary embodiment of the present disclosure.

The ability of this contrast to provide visualization of the gallbladder and cystic ducts was also evaluated in the pigs. Delineation between the gallbladder, cystic ducts, and cystic artery can be observed via fluorescence in FIG. 15.

Figure 16:
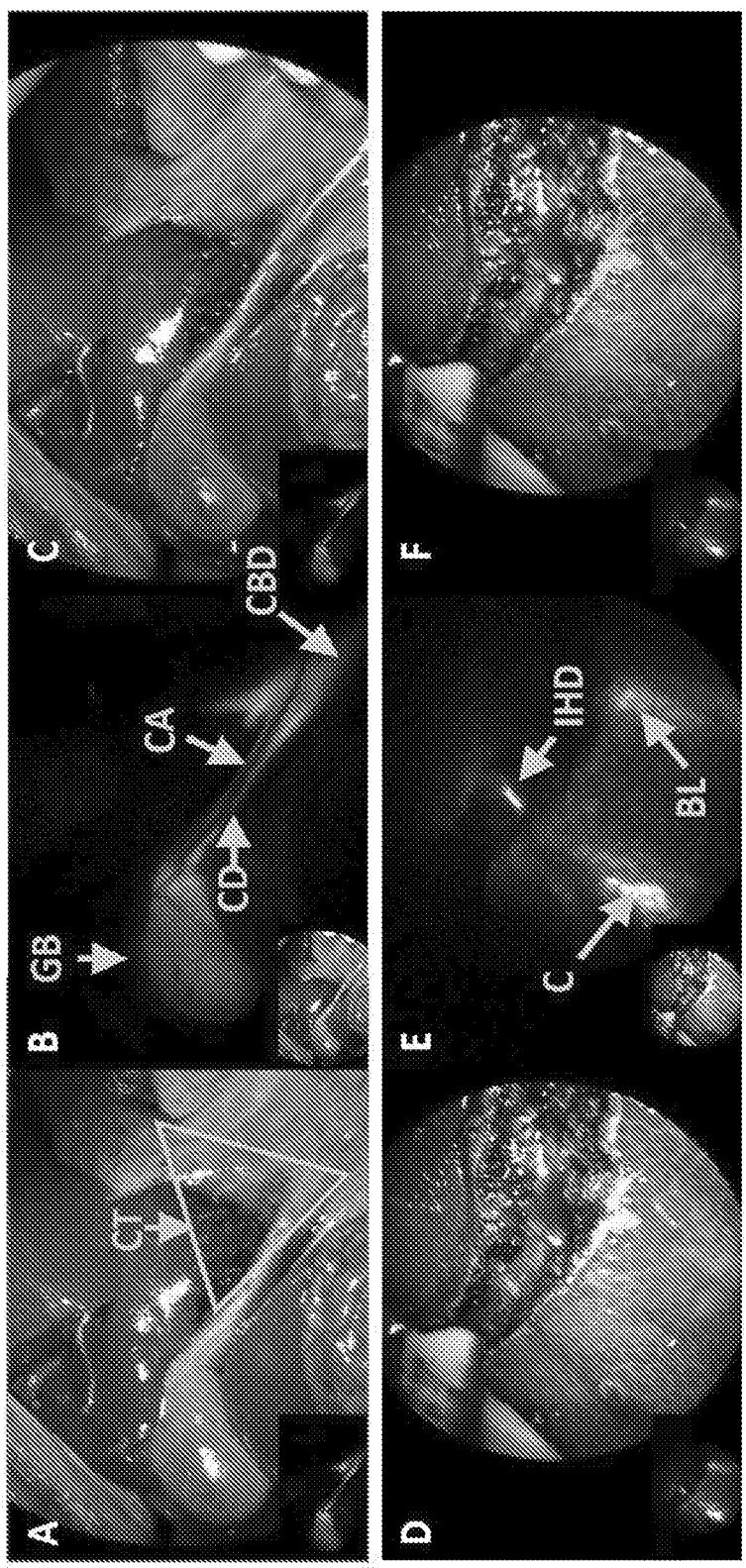
FIG. 16 is a panel of illustrations demonstrating the visualization of Calot's triangle, according to an exemplary embodiment of the present disclosure.

After careful dissection of the liver hilium, Calot's triangle was exposed and visualized successfully, as depicted in FIG. 16. In addition, a left lobectomy was performed. After liver resection, intrahepatic ducts were exposed and highlighted with fluorescent signals, as FIG. 16. Further, during the procedure, small holes were created in the liver parenchyma and bile leakage was easily detected, as shown.

During hepatectomy, BL-760 allowed for differentiation of Glisson from the hepatic vein. BL-760 permitted identification of unexpected biliary tract anatomy during surgery.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A compound or a stereoisomer thereof according to Formula I:

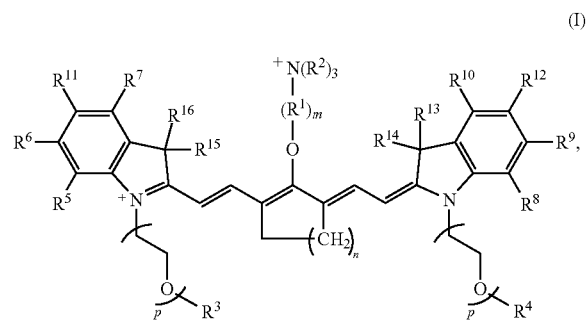

(I)

wherein m is 3, 4, or 5, n is 1, 2, or 3, each p independently is 1, 2, 3, 4, 5, 6, 7, 8, 9, or 10, $R^1$ is —$CR^a{}_2$— where each $R^a$ independently is H, halo, optionally substituted alkyl, or optionally substituted aryl, each $R^2$ independently is methyl, ethyl, n-propyl, or isopropyl, $R^3$ and $R^4$ independently are alkyl, $R^5$ to $R^{10}$ independently are H or alkyl, $R^{11}$ and $R^{12}$ independently are sulfonate, H, or alkyl, and $R^{13}$ to $R^{16}$ independently are alkyl.

(2) The compound according to (1), wherein $R^3$ and $R^4$ are the same, $R^5$ and $R^8$ are the same, $R^6$ and $R^9$ are the same, $R^7$ and $R^{10}$ are the same, $R^{11}$ and $R^{12}$ are the same, and $R^{13}$-$R^{16}$ are the same.

(3) The compound according to either (1) or (2), wherein p is 2, 3, or 4.

(4) The compound according to any of (1) to (3), wherein the compound is Formula IA:

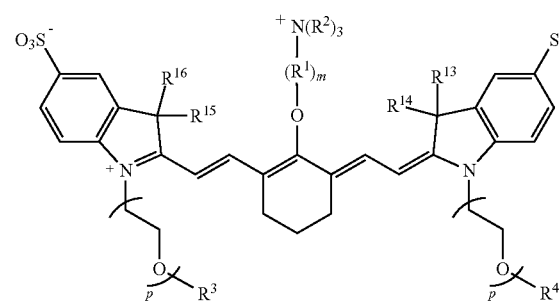

(IA)

$R^1$ is —$CH_2$—, m is 3, and p is 2, 3, or 4.

(5) The compound according to any of (1) to (4), wherein at least one of $R^3$ and $R^4$ are methyl, and $R^{13}$-$R^{16}$ are methyl.

(6) A compound or a stereoisomer thereof according to Formula II:

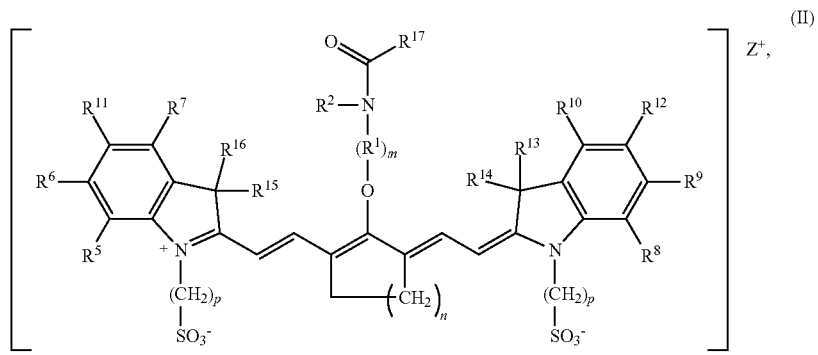

(II)

wherein m is 2, 3, 4, or 5, n is 1, 2, or 3, each p independently is 1, 2, 3, 4, 5, 6, 7, 8, 9, or 10, $R^1$ is —$CR^a_2$— where each $R^a$ independently is H, halo, optionally substituted alkyl, or optionally substituted aryl, $R^2$ is $C_1$-$C_3$ alkyl, $R^5$ to $R^{12}$ independently are H or alkyl, $R^{13}$ to $R^{16}$ independently are alkyl, $R^{17}$ is $C_1$-$C_3$ alkyl, and Z is a monatomic ion.

(7) The compound according to (6), wherein $R^5$ and $R^8$ are the same, $R^6$ and $R^9$ are the same, $R^7$ and $R^{10}$ are the same, $R^{11}$ and $R^{12}$ are the same, and $R^{13}$-$R^{16}$ are the same.

(8) The compound according to either (6) or (7), wherein p is 3, 4, or 5.

(9) The compound according to any of (6) to (8), wherein the compound is Formula IIA:

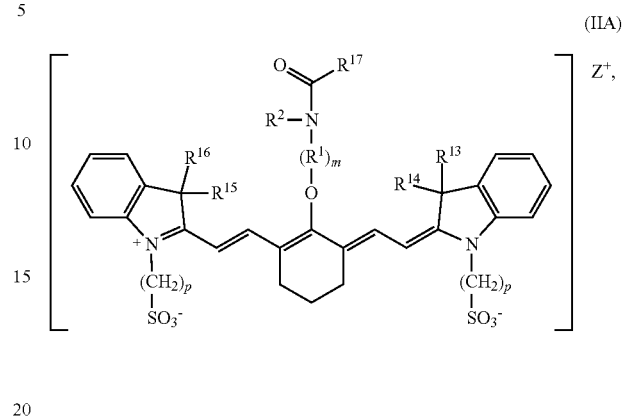

(IIA)

$R^1$ is —$CH_2$—, m is 2, and p is 3, 4, or 5.

(10) The compound according to any of (6) to (9), wherein at least one of $R^{17}$ is methyl or ethyl, and $R^{13}$ to $R^{16}$ are methyl.

(11) The compound according to any of (1) to (5), wherein each $R^2$ independently is methyl or ethyl.

(12) The compound according to any of claim (6) to (10), wherein each $R^2$ independently is methyl or ethyl.

(13) The compound according to any of (1) to (5), wherein the compound is

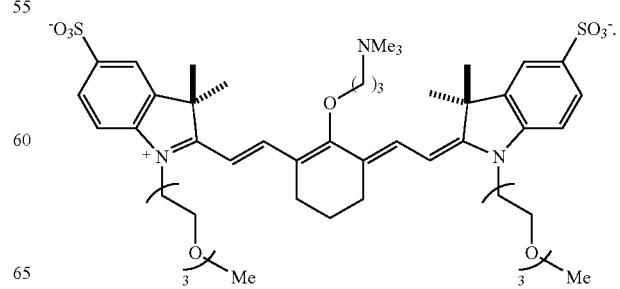

(14) The compound according to any of (6) to (10), wherein the compound is

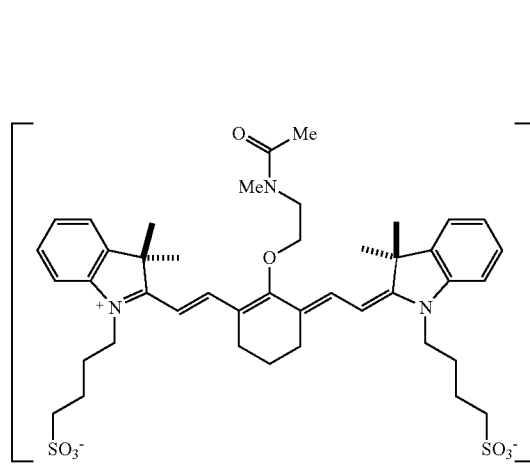

(15) A pharmaceutical composition, comprising a compound according to any of (1) to (5), and a pharmaceutically acceptable carrier.

(16) A pharmaceutical composition, comprising a compound according to any of (6) to (10), and a pharmaceutically acceptable carrier.

(17) A method for visualizing at least a portion of a renal system or a biliary system of a subject, the method comprising administering to the subject a compound, subsequently administering a quantity of light to a targeted portion of the subject, wherein the quantity of light has a wavelength and an intensity sufficient to produce fluorescence of the compound, and detecting fluorescence in the targeted portion of the subject, wherein fluorescence indicates presence of the compound in the targeted portion of the subject.

(18) The method according to (17), wherein the compound is

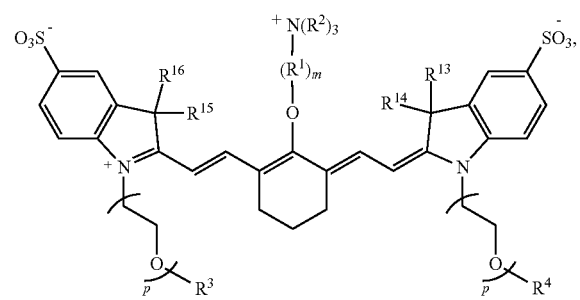

$R^1$ is —$CH_2$—, m is 3, and p is 2, 3, or 4.

(19) The method according to either (17) or (18), wherein the compound is

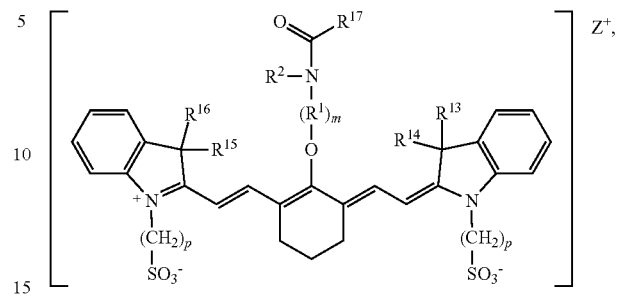

$R^1$ is —$CH_2$—, m is 2, and p is 3, 4, or 5.

(20) The method according to any of (17) to (19), wherein the compound is

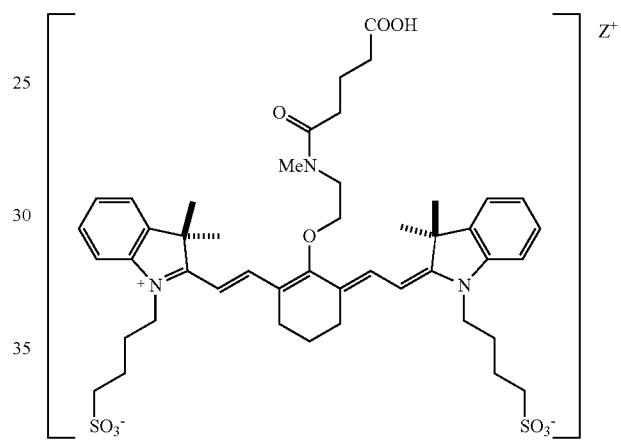

and Z is a monatomic ion.

(21) The method according to any of (17) to (20), wherein the light has a wavelength or a range of wavelengths in the near-infrared range.

(22) The method according to any of (17) to (21), wherein the targeted portion of the subject comprises at least a portion of the renal system.

(23) The method according to any of (17) to (22), wherein the light has a wavelength within a range of from 760-780 nm.

(24) The method according to (17), wherein the compound is

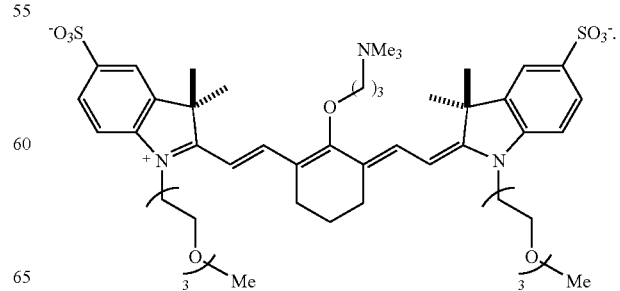

(25) The method according to (17), wherein the compound is one selected from a group including

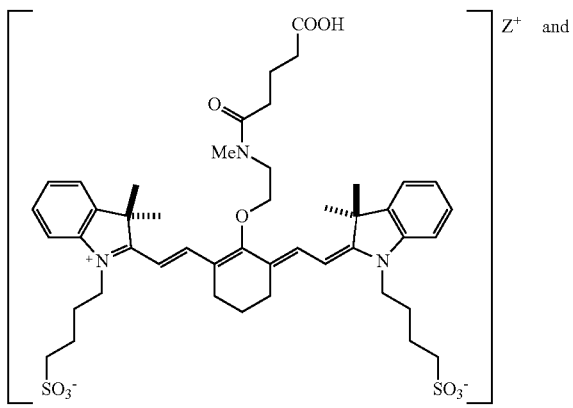

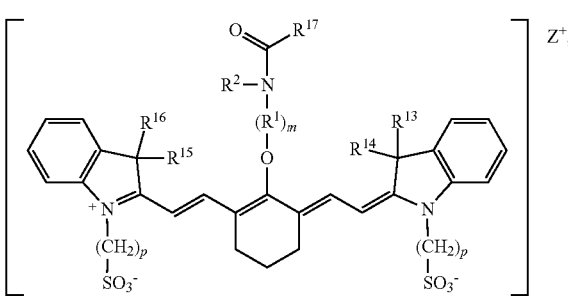

$R^1$ is —CH$_2$—, m is 2, p is 3, 4, or 5, and the targeted portion of the subject comprises at least a portion of the biliary system.

(26) The method according to either (17) or (25), wherein the light has a wavelength within a range of from 600-850 nm.

(27) The method according to either (17) or (25), wherein the compound is

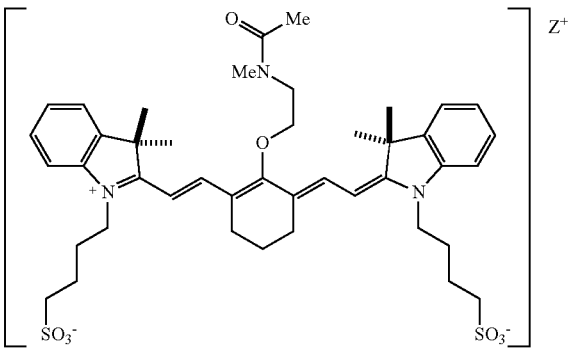

(28) A method for visualizing at least a portion of a renal system of a patient, the method comprising administering to the patient a compound, subsequently administering a quantity of light to a ureteropelvic junction of the patient, wherein the quantity of light has a wavelength and an intensity sufficient to produce fluorescence of the compound, detecting fluorescence in the ureteropelvic junction of the patient, wherein fluorescence indicates presence of the compound in the ureteropelvic junction of the patient, and determining, based on the detecting of the fluorescence in the ureteropelvic junction of the patient, an obstruction of a ureter, wherein the compound is

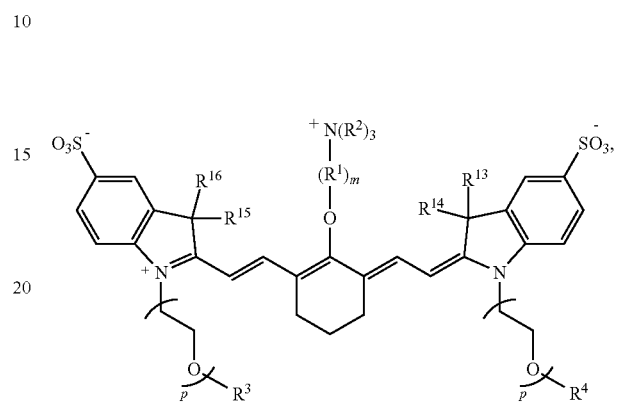

$R^1$ is —CH$_2$—, m is 3, and p is 2, 3, or 4.

(29) A method for visualizing at least a portion of a biliary system of a patient, the method comprising administering to the patient a compound, subsequently administering a quantity of light to the biliary system of the patient, wherein the quantity of light has a wavelength and an intensity sufficient to produce fluorescence of the compound, detecting fluorescence in the biliary system of the patient, wherein fluorescence indicates presence of the compound in the biliary system of the patient, and determining, based on the detecting of the fluorescence in the biliary system of the patient, bile leakage from a bile duct of the biliary system, wherein the compound is

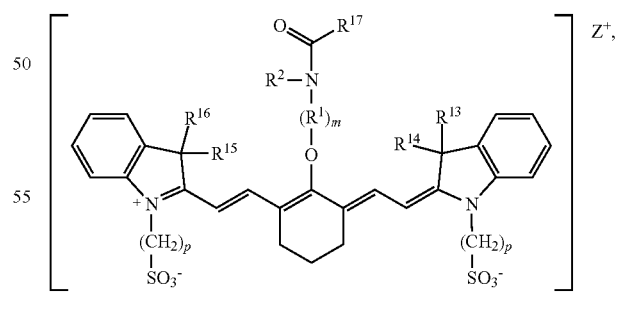

$R^1$ is —CH$_2$—, m is 2, and p is 3, 4, or 5.

(30) A method for visualizing at least a portion of a biliary system of a patient, the method comprising administering to the patient a compound, subsequently administering a quantity of light to the biliary system of the patient, wherein the quantity of light has a wavelength and an intensity sufficient to produce fluorescence of the compound, detecting fluorescence in the biliary system of the patient, wherein fluorescence indicates presence of the compound in the biliary system of the patient, and determining, based on the detecting of the fluorescence in the biliary system of the patient, bile leakage from a bile duct of the biliary system, wherein the compound is

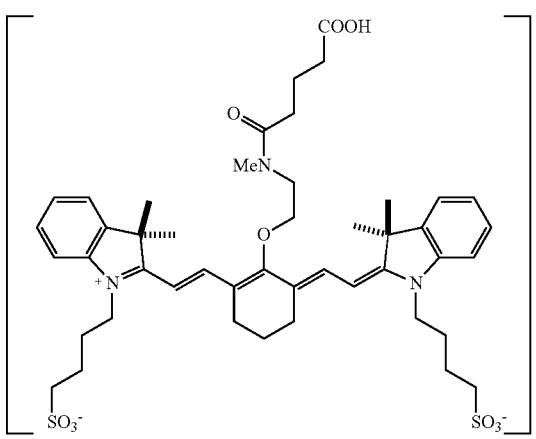

and Z is a monatomic ion.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for in vivo visualization of a renal system, comprising:
   (i) administering to the subject a pharmaceutical composition comprising a fluorescence agent comprising a compound of Formula IA in an amount sufficient to effect fluorescence detection of the portion of the renal system upon irradiation with light having a wavelength in the range of 650 nm to 900 nm:

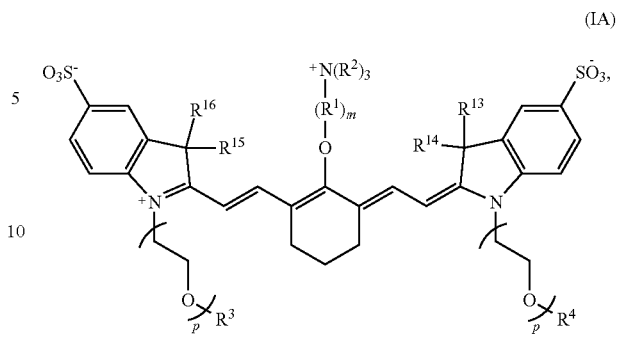

wherein
   $R^1$ is —$CH_2$—,
   each $R^2$ independently is methyl, ethyl, n-propyl, or isopropyl,
   $R^3$ and $R^4$ independently are $C_1$-$C_{10}$ alkyl,
   $R^{13}$ $R^{16}$ independently are $C_1$-$C_{10}$ alkyl,
   m is 3, and
   p is 2, 3, or 4;
   (ii) allowing time following the administration for accumulation of the compound of Formula IA in the renal system;
   (iii) irradiating the renal system with light having a wavelength in the range of 650 nm to 900 nm (NIR) to produce a fluorescence signal of the compound of Formula IA in the renal system;
   iv) visualizing at least one portion of the renal system by detection of the fluorescence signal produced upon the irradiation (iii);
   wherein
   a contrast to background ratio (CBR) of the fluorescence signal to a background signal in a region of the renal system being visualized is 1.5 or more within 20 minutes of the administration.

2. The method according to claim 1, wherein administering the pharmaceutical composition comprises at least one route selected from the group consisting of oral, buccal, systemic, injection, transdermal, rectal, inhalation and insufflation.

3. The method according to claim 1, wherein the CBR remains 1.5 or more for at least 30 minutes.

4. The method according to claim 1, wherein the pharmaceutical composition further comprises at least one selected from the group consisting of a pharmaceutically and physiologically acceptable fluid, an excipient. a non-toxic wetting agent, a non-toxic emulsifying agent, a preservative and a pH buffering agent.

5. The method according to claim 1, wherein the light source for irradiating the target system is selected from the group consisting of a laser, a light-emitting diode (LED), a xenon lamp, a halogen bulb and a vertical-cavity surface-emitting laser (VSCEL).

6. The method according to claim 1, wherein the effective amount of the compound of Formula IA is from 1 µg/kg to 240 µg/kg body weight of the subject.

7. The method according to claim 1, wherein an effective quantity of NIR light irradiating the target system is from 0.1 to 1000 mW/cm².

8. The method according to claim 1 wherein the fluorescence agent consists of the compound of Formula IA.

9. The method according to claim 1, wherein
the irradiation is performed externally with a light applicator selected from the group consisting of a microlens, a Fresnel lens and a diffuser, or
the irradiation is performed internally with an endoscope or a fiber optic catheter.

10. The method according to claim 1 wherein the compound of Formula IA is the compound of the formula UL-766:

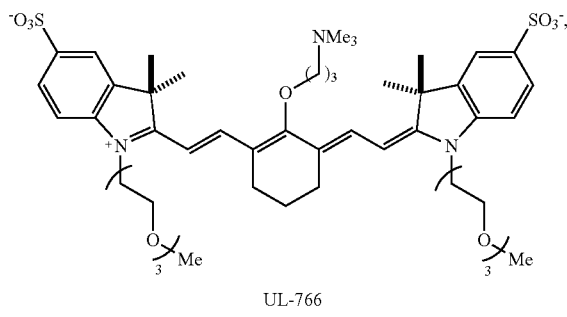

UL-766 and the NIR is of a wavelength ranging from 600 nm to 850 nm.

11. The method according to claim 10, wherein a biliary:urinary specificity of the compound UL-766 is 5:95.

12. A surgical procedure within the abdominopelvic area. of a patient, comprising:
administering to the patient a pharmaceutical composition comprising the compound UL-766;
allowing time for the compound UL-766 to accumulate in the ureter;
irradiating the abdominopelvic area with NIR of a wavelength from 600 nm to 850 nm to visualize the ureter by fluorescence of the UL-766 accumulated in the ureter; and
performing surgery within the abdominopelvic area during the visualization of the ureter;

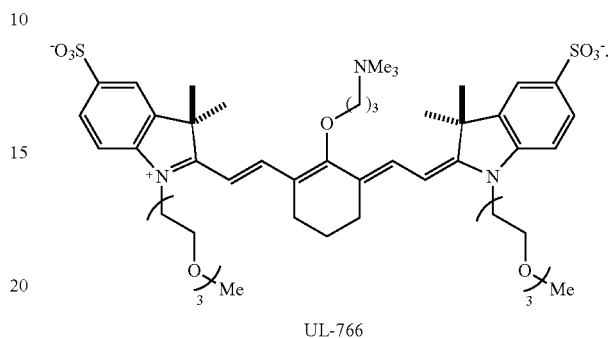

UL-766

13. The surgical procedure according to claim 12, wherein the surgical procedure is an open surgery, a laparoscopic procedure or an endoscopic procedure.

14. The surgical procedure according to claim 12, wherein the abdominopelvic surgical procedure is a gynecologic procedure, an obstetric procedure, a general surgical procedure or a urologic procedure.

* * * * *